(12) United States Patent
Barrow et al.

(10) Patent No.: US 8,637,513 B2
(45) Date of Patent: Jan. 28, 2014

(54) HETEROCYCLE PHENYL AMIDE T-TYPE CALCIUM CHANNEL ANTAGONISTS

(75) Inventors: James C. Barrow, Harleysville, PA (US); Paul J. Coleman, Wallingford, PA (US); Thomas S. Reger, Lansdale, PA (US); Kelly-Ann S. Schlegel, Fleetwood, PA (US); Youheng Shu, Blue Bell, PA (US); Zhi-Qiang Yang, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 560 days.

(21) Appl. No.: 12/739,294

(22) PCT Filed: Oct. 23, 2008

(86) PCT No.: PCT/US2008/012039
§ 371 (c)(1),
(2), (4) Date: Apr. 22, 2010

(87) PCT Pub. No.: WO2009/054984
PCT Pub. Date: Apr. 30, 2009

(65) Prior Publication Data
US 2010/0261724 A1    Oct. 14, 2010

Related U.S. Application Data

(60) Provisional application No. 61/000,156, filed on Oct. 24, 2007, provisional application No. 61/072,568, filed on Apr. 1, 2008.

(51) Int. Cl.
| | | |
|---|---|---|
| *C07D 401/12* | (2006.01) |
| *A61K 31/517* | (2006.01) |
| *A61K 31/497* | (2006.01) |
| *A61K 31/4439* | (2006.01) |
| *C07D 487/04* | (2006.01) |
| *A61K 31/5025* | (2006.01) |
| *C07D 413/12* | (2006.01) |
| *A61K 31/443* | (2006.01) |
| *C07D 417/12* | (2006.01) |
| *A61K 31/4436* | (2006.01) |
| *C07D 213/63* | (2006.01) |
| *C07D 239/74* | (2006.01) |
| *C07D 241/36* | (2006.01) |
| *C07D 471/02* | (2006.01) |
| *A61P 25/08* | (2006.01) |
| *A61P 29/00* | (2006.01) |
| *A61P 25/18* | (2006.01) |
| *A61P 25/16* | (2006.01) |
| *A61P 25/24* | (2006.01) |
| *A61P 25/22* | (2006.01) |
| *A61P 9/08* | (2006.01) |
| *A61P 9/12* | (2006.01) |
| *A61P 35/00* | (2006.01) |
| *A61P 31/10* | (2006.01) |

(52) U.S. Cl.
USPC .......... 514/248; 514/252.1; 514/255.05; 514/339; 514/336; 514/342; 514/338; 514/303; 514/300; 544/284; 544/405; 544/236; 544/253; 544/353; 546/277.4; 546/272.1; 546/340; 546/278.4; 546/275.7; 546/261; 546/122

(58) Field of Classification Search
USPC ............ 544/235, 284, 405, 236, 253, 353; 514/248, 258.1, 255.05, 339.248, 336, 514/342, 338, 303, 300; 546/277.4, 272.1, 546/340, 278.4, 269.7, 275.7, 261.122
See application file for complete search history.

(56) References Cited

U.S. PATENT DOCUMENTS

| 2,798,075 A | 7/1957 | Bellet |
| 3,594,982 A | 7/1971 | Florin et al. |

(Continued)

FOREIGN PATENT DOCUMENTS

| EP | 1 760 072 | 3/2007 |
| EP | 1 762 218 | 3/2007 |

(Continued)

OTHER PUBLICATIONS

Khosravani, et al., Journal of Biological Chemistry vol. 279, No. 11, Issue of Mar. 12, pp. 9681-9684, 2004.*

(Continued)

*Primary Examiner* — James O Wilson
*Assistant Examiner* — Cecilia M Jaisle
(74) *Attorney, Agent, or Firm* — J. Eric Thies; John C. Todaro

(57) ABSTRACT

The present invention is directed to heterocycle phenyl amide compounds which are antagonists of T-type calcium channels, and which are useful in the treatment or prevention of disorders and diseases in which T-type calcium channels are involved. The invention is also directed to pharmaceutical compositions comprising these compounds and the use of these compounds and compositions in the prevention or treatment of such diseases in which T-type calcium channels are involved.

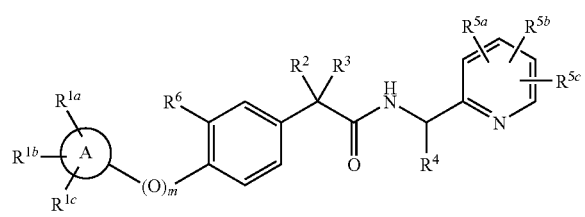

12 Claims, No Drawings

(56) References Cited

U.S. PATENT DOCUMENTS

| | | | |
|---|---|---|---|
| 3,679,698 | A | 7/1972 | Gamaliel et al. |
| 5,607,976 | A | 3/1997 | Englert et al. |
| 5,693,650 | A | 12/1997 | Muller et al. |
| 5,747,505 | A | 5/1998 | Connell et al. |
| 5,925,646 | A | 7/1999 | Connell et al. |
| 6,521,663 | B2 | 2/2003 | Pan et al. |
| 6,703,392 | B2 | 3/2004 | Aissaoui et al. |
| 6,897,207 | B2 | 5/2005 | Cox et al. |
| 6,900,231 | B2 | 5/2005 | Pan et al. |
| 6,989,402 | B1 | 1/2006 | Hangeland et al. |
| 7,192,950 | B2 | 3/2007 | Aissaoui et al. |
| 7,288,571 | B2 | 10/2007 | Hangeland et al. |
| 7,767,675 | B2 | 8/2010 | Zhuo et al. |
| 7,875,636 | B2 | 1/2011 | Barrow et al. |
| 2002/0183519 | A1 | 12/2002 | Nar et al. |
| 2002/0193398 | A1 | 12/2002 | Barrow et al. |
| 2003/0100554 | A1 | 5/2003 | Jones et al. |
| 2003/0199523 | A1 | 10/2003 | Snutch |
| 2006/0074076 | A1 | 4/2006 | Termin et al. |
| 2007/0043038 | A1 | 2/2007 | Starck et al. |
| 2007/0173504 | A1 | 7/2007 | Pacofsky et al. |
| 2007/0270428 | A1* | 11/2007 | Hagan et al. ............... 514/248 |
| 2008/0039472 | A1 | 2/2008 | Lacrampe et al. |
| 2008/0167287 | A1 | 7/2008 | Zhuo et al. |
| 2008/0318976 | A1 | 12/2008 | Wood et al. |
| 2009/0275550 | A1 | 11/2009 | Barrow et al. |
| 2010/0222387 | A1 | 9/2010 | Barrow et al. |
| 2010/0256156 | A1* | 10/2010 | Banno et al. ............ 514/252.01 |
| 2011/0034378 | A1* | 2/2011 | Dutt et al. ................... 514/6.5 |
| 2011/0039873 | A1* | 2/2011 | Gaeta et al. .................. 514/275 |
| 2011/0059946 | A1* | 3/2011 | Hubschwerlen et al. 514/210.21 |
| 2011/0071149 | A1* | 3/2011 | Ma et al. ................... 514/234.8 |
| 2011/0112064 | A1 | 5/2011 | Barrow et al. |
| 2011/0136781 | A1 | 6/2011 | Zhuo et al. |
| 2011/0205015 | A1* | 8/2011 | Finkenzeller et al. ......... 340/5.8 |
| 2011/0251226 | A1* | 10/2011 | Plettenburg et al. .......... 514/248 |
| 2011/0319379 | A1* | 12/2011 | Corbett et al. ........... 514/210.18 |
| 2012/0016119 | A1* | 1/2012 | Tsuboi et al. .................. 544/117 |
| 2012/0022083 | A1* | 1/2012 | Gupta et al. ............. 514/255.05 |
| 2012/0029016 | A1* | 2/2012 | Nilsson ......................... 514/314 |
| 2012/0029026 | A1* | 2/2012 | Shinozuka et al. ........... 514/338 |
| 2012/0046294 | A1* | 2/2012 | Kadow et al. ................. 514/248 |
| 2012/0046300 | A1* | 2/2012 | Hennequin .............. 514/252.17 |
| 2012/0088763 | A1* | 4/2012 | Finch et al. ................. 514/232.5 |

FOREIGN PATENT DOCUMENTS

| | | |
|---|---|---|
| FR | 2 751 970 | 2/1998 |
| GB | 782 067 | 8/1957 |
| GB | 1 403 264 | 8/1975 |
| JP | 10 101658 | 4/1998 |
| WO | WO93/09077 | 5/1993 |
| WO | WO9821185 | 5/1998 |
| WO | WO0111966 | 2/2001 |
| WO | WO0168609 | 9/2001 |
| WO | WO02051838 | 7/2002 |
| WO | WO02062778 | 8/2002 |
| WO | WO03000688 | 1/2003 |
| WO | WO2006021256 | 3/2006 |
| WO | WO2006032631 | 3/2006 |
| WO | WO2006115652 | 11/2006 |
| WO | WO2007/002361 | 1/2007 |
| WO | WO2007073505 | 6/2007 |
| WO | WO2007/120729 | 10/2007 |
| WO | WO2008/064157 | 5/2008 |
| WO | WO2009054982 | 4/2009 |
| WO | WO2009054983 | 4/2009 |
| WO | WO2009054984 | 4/2009 |

OTHER PUBLICATIONS

Dogrul, et al., Pain 105 (2003) 159-168.*
Lee, et al., Bull. Korean Chem. Soc. 2010, vol. 31, No. 9 2451.*
Ethosuximide, http://en.wikipedia.org/wiki/Ethosuximide, last modified on Apr. 25, 2012.*
G. Primofiore et al., "Refinement of the Benzodiazepine Receptor Site Topology by Structure-Activity Relationships of New N-(Heteroarylmethyl) Indo)-3-Y 1glyoxylamides", J. of Medicinal Chemistry, vol. 49, No. 8, pp. 2489-2495,.
P. G. Nantermet et al., "P2 Pyridine N-Oxide Thrombin Inhibitors: A Novle Peptidomimetic Scaffold", Biorganic & Medicinal Chemistry Letters, vol. 15, No. 11, pp. 2771-2775, XP004906893, 2005.
Hanessian et al., "Phenolic P2/P3 Core Motif as Thrombin Inhibitors-Desing, Synthesis, and X-Ray Co-Crystal Structure", Biorganic & Medicinal Chemistry Letters, vol. 16, No. 4, pp. 1032-1036, XP005237642, 2006.
Data Beilstein, Beilstein Institute for Organic Chemistry, Frankfurt-Main, DE: BRN 6741916, XP002457570, 1983.
Y. Katsura et al., "Thiazoline or Thiazine Derivatives as Nitric Oxide Formation Inhibitors", Database Accession No. 1998:239552, XP002457571, 1998.
Howell et al., "Synthesis and Characterization of 3-Thiophene Carboxamides Containing a Pyridine Ring: Structure, Electrochemistry, and Complexation", vol. 358, No. 13, pp. 3711-3723, XP005065590, 2005.
G. Blay et al., "Catalytic Asymmetric Addition of Dimethyizinc to Alpha-Ketoesters, Using Mandelamides as Ligands", Database Accession No. 2006:207062, XP002457572, 2006.
G. Blay et al., "Enantioselective Additon of Dimethylzinc to Aldehydes Catalyzed by N-Substituted Mandelamide—Ti (IV) Complexes", vol. 16, No. 11, pp. 1953-1958, XP00492366, 2005.
W. L. Albrecht et al., "3-Substituted Imidazoa1, 5-Alphaupyridines" J. of Heterocyclic Chemistry, vol. 16, No. 7. pp. 1349-1351, XP001106066, 1979.
K. Winterfield et al., "Synthesis of 3-Substittued 2-Azainolizines", vol. 75, No. 22, pp. 1101-1102, XP002457569, 1963.
B. Lee et al., "Copper (II) Complexes with Novel Chiral Amidate Ligands", Database Accession No. 2002:100958, 2002.
E. Widy-Tyszkiewicz et al., "Pharmacological Studies on 2-and 4-Pyridylmethylamides of Acetyltropic Acid (PAT-2 and PAT-4")", Database Accession No. 1975:601828, 1975.
N. Nonoyama et al., "Cobalt (II), Nickel (II), and Copper (II) Complexes of Potentially Terdentate N-(2'-Picolyl)-2-PYridylacetamide", Database Accession No. 1975:557164, 1975.
V. Uebele et al., "Positive Allosteric Interaction of Structurally Diverse T-Type Calcium Channel Antagonists", Cell Biochem Biophys, pp. vol. 55, pp. 81-93, 2009,.
V. Uebele et al., "T-Type Calcium Channels Regulate Cortical Plasticity In-Vivo NR-D-08-7049", Neurophysiology, vol. 20, pp. 257-262, 2009.
International Search Report, PCT/US2007/008977,Nov. 15, 2007.
International Preliminary Report on Patentability, PCT/US2007/008977, Oct. 23, 2008.
International Preliminary Report on Patentability, PCT/US2008/012039, Apr. 27, 2010.
J. M. Uslaner et al. "T-Type Calcium Channel Antagonism Produces Antipsyhcotic-Like Efects and Reduces Stimulant-Induced Glutamate Release in the Nucleus Accumbens of Rats", Neuropharmacology, 1-9 (Nov. 24, 2010).
R. L. Kraus et al., "In Vitro Characterization of T-Type Calcium Channel Antagonist TTA-A2 and in Vivo Effects on Arousal in Mice", J. Pharmacol. Exp. Ther 335, pp. 409-417, 2010.
Database Registry, "Benzeneacetamide, 4-[[3-[(4-fluorophenyl)methly]-1,2,4-thiadiazol-5-y]oxyl]-N-(2-pyridinylmethyl)", Registry No. 855509-20-5:, XP002513628, Jul. 15, 2005.
Database Registry, "4-[[3-[[(3-methoxyphenyl)methyl]-1,2,4-thiadiazol-5-yl]oxyl]-N-(2-pyridinylmethyl)-"Registry No. 854170-18-6:, XP002513629, Jul. 8, 2005.
Database Registry, "4-(1,4-dihydro-4-oxo-2-thioxo-3(2H)-quinazolinyl)-N-(2-pyridinylmethyl)", Registry No. 689763-76-6, XP002513630, Jun. 6, 2004.
Database Registry, "4-(2-methyl-3H-Imidazo(4,5-b)pyridin-3-yl)-N-(2-pyridinylmethyl)", Registry No. 931970-35-3, XP002513623, Apr. 23, 2007.

(56) References Cited

OTHER PUBLICATIONS

Database Registry, "4-(1,4-Dihydro-2,4-Dioxo-3(2H)-quinazoliny 1)-N-(2-pyridinylmethyl", Registry No. 896376-19-5, XP00251624, Jul. 27, 2006.

Database Registry, "Benzeneacetamide, 4-[(2-ethyl-3H-imidazo[4,5-b]pyridin-3-yl)-N-(2-pyridinylmethyl)", Registry No. 894181-12-5, XP002513625, Jul. 18, 2006.

Database Registry, "Benzeneacetamide, 4-(2-oxo-1-pyrrolidinyl)-N-(2-pyridinylmethyl)", Registry No. 931630-57-8, XP002513626, Apr. 22, 2007.

Database Registry, "Benzeneacetamide, 4-[[3-(phenylmethyl)-1,2,4-thiadiazol-5-yl]oxy]-N-(2-pyridinylmethyl)", Registry No. 857861-48-4, XP002513627, Aug. 1, 2005.

* cited by examiner

HETEROCYCLE PHENYL AMIDE T-TYPE CALCIUM CHANNEL ANTAGONISTS

CROSS REFERENCE TO RELATED APPLICATIONS

This application is a U.S. National Phase application under 35 U.S.C. §371 of PCT Application No. PCT/US2008/012039, filed Oct. 23, 2008, which claims priority under 35 U.S.C. §119(e) from U.S. Ser. No. 61/000,156, filed Oct. 24, 2007 and 61/072,568 filed Apr. 1, 2008.

BACKGROUND OF THE INVENTION

Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels Multiple types of calcium channels have been identified in mammalian cells from various tissues, including skeletal muscle, cardiac muscle, lung, smooth muscle and brain. A major type of this family are the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T, N, P, Q and R.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties. There are three subtypes of T-type calcium channels that have been molecularly, pharmacologically, and electrophysiologically identified from various warm blooded animals including rat [J. Biol. Chem. 276(6) 3999-4011 (2001); Eur J Neurosci 11(12):4171-8 (1999); reviewed in Cell Mol Life Sci 56(7-8):660-9 (1999)]. These subtypes have been termed al G, α1H, and α1I. The molecular properties of these channels demonstrate that the amino acid sequences are between 60-70% identical. The electrophysiological characterization of these individual subtypes has revealed differences in their voltage-dependent activation, inactivation, deactivation and steady-state inactivation levels and their selectivities to various ions such as barium (J. Biol. Chem. 276(6) 3999-4011 (2001)). Pharmacologically, these subtypes also have differing sensitivities to blockade by ionic nickel. These channel subtypes are also expressed in various forms due to their ability to undergo various splicing events during their assembly (J. Biol. Chem. 276(6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, pain, cancer, diabetes, infertility and sexual dysfunction (J Neuroscience, 14, 5485 (1994); Drugs Future 30(6), 573-580 (2005); EMBO J, 24, 315-324 (2005); Drug Discovery Today, 11, 5/6, 245-253 (2006)). The known therapeutic regimens for such treating such diseases and disorders suffer from numerous problems. Accordingly, a more physiological way to treat these diseases and disorders would be highly desirable.

SUMMARY OF THE INVENTION

The present invention is directed to heterocycle phenyl amide compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

DETAILED DESCRIPTION OF THE INVENTION

The present invention is directed to compounds of the formula I:

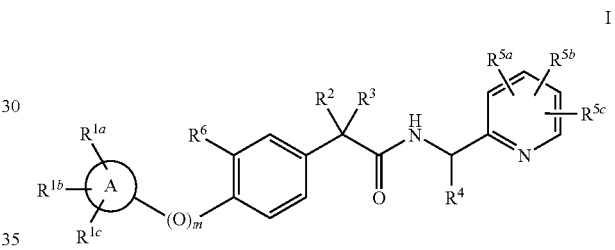

wherein:
A is a heterocycle;
m is 0 or 1 (wherein if m is 0, a bond is present);
$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —$O_n$-phenyl or —$O_n$-napthyl, where n is 0 or 1 (wherein if n is 0, a bond is present) and where the phenyl or napthyl is unsubstituted or substituted with one or more substituents selected from $R^{13}$,
(5) —$O_n$-heterocycle, where n is 0 or 1 (wherein if n is 0, a bond is present) and where the heterocycle is unsubstituted or substituted with one or more substituents selected from $R^{13}$,
(6) —$O_n$—$C_{1-6}$alkyl, where n is 0 or 1 (wherein if n is 0, a bond is present) and where the alkyl is unsubstituted or substituted with one or more substituents selected from $R^{13}$,
(7) —$O_n$—$C_{3-6}$cycloalkyl, where n is 0 or 1 (wherein if n is 0, a bond is present) and where the cycloalkyl is unsubstituted or substituted with one or more substituents selected from $R^{13}$,
(8) —$C_{2-4}$alkenyl, where the alkenyl is unsubstituted or substituted with one or more substituents selected from $R^{13}$,
(9) —$NR^{10}R^{11}$, wherein $R^{10}$ and $R^{11}$ are independently selected from the group consisting of:

(a) hydrogen,
(b) $C_{1-6}$alkyl, which is unsubstituted or substituted with $R^{13}$,
(c) $C_{3-6}$alkenyl, which is unsubstituted or substituted with $R^{13}$,
(d) cycloalkyl which is unsubstituted or substituted with $R^{13}$,
(e) phenyl, which is unsubstituted or substituted with $R^{13}$, and
(f) heterocycle, which is unsubstituted or substituted with $R^{13}$,
or $R^{10}$ and $R^{11}$ taken together with the nitrogen atom to which they are attached form a pyrrolidine, piperidine, azetidine or morpholine ring, which is unsubstituted or substituted with $R^{13}$,
(10) —S(O)$_2$—NR$^{10}$R$^{11}$,
(11) —S(O)$_q$—R$^{12}$, where q is 0, 1 or 2 and where $R^{12}$ is selected from the definitions of $R^{10}$ and $R^{11}$,
(12) —CO$_2$H,
(13) —CO$_2$—R$^{12}$,
(14) —CN, and
(15) —NO$_2$;
or $R^{1a}$ and $R^{1b}$ taken together form a cyclopentyl, cyclohexyl, dihydrofuranyl or dihydropyranyl ring, which is unsubstituted or substituted with one or more substituents selected from —CH$_3$, (=CH$_2$), keto, and hydroxyl;

$R^2$ and $R^3$ are independently selected from the group consisting of:
(1) hydrogen,
(2) hydroxyl,
(3) halogen
(4) $C_{1-6}$alkyl, which is unsubstituted or substituted with one or more substituents selected from $R^{13}$,
(5) $C_{3-6}$cycloalkyl, which is unsubstituted or substituted with one or more substituents selected from $R^{13}$,
(6) —O—$C_{1-6}$alkyl, which is unsubstituted or substituted with one or more substituents selected from $R^{13}$,
(7) —O—$C_{3-6}$cycloallyl, which is unsubstituted or substituted with one or more substituents selected from $R^{13}$,
or $R^2$ and $R^3$ and the carbon atom to which they are attached form a keto group,
or $R^2$ and $R^3$ and the carbon atom to which they are attached form a $C_{3-6}$cycloalkyl ring, which is unsubstituted or substituted with $R^{13}$;

$R^4$ is selected from the group consisting of:
(1) hydrogen,
(2) $C_{1-6}$alkyl, which is unsubstituted or substituted with one or more substituents selected from $R^{13}$,
(3) —$C_{3-6}$cycloalkyl, which is unsubstituted or substituted with one or more substituents selected from $R^{13}$,
(4) $C_{2-6}$alkenyl, which is unsubstituted or substituted with one or more substituents selected from $R^{13}$,
(5) $C_{2-6}$alkynyl, which is unsubstituted or substituted with one or more substituents selected from $R^{13}$,
(6) phenyl, which is unsubstituted or substituted with one or more substituents selected from $R^{13}$,
(7) —(C=O)—NR$^{10}$R$^{11}$, and
(8) —(C=O)—O—$C_{1-6}$alkyl, which is unsubstituted or substituted with one or more substituents selected from $R^{13}$, $R^{5a}$, $R^{5b}$ and $R^{5c}$ are independently selected from the group consisting of:
(1) hydrogen,
(2) halogen,
(3) hydroxyl,
(4) —O$_n$—$C_{1-6}$alkyl, where n is 0 or 1 (wherein if n is 0, a bond is present) and where the alkyl is unsubstituted or substituted with one or more substituents selected from $R^{13}$,
(5) —O$_n$—$C_{3-6}$cycloalkyl, where n is 0 or 1 (wherein if n is 0, a bond is present) and where the cycloalkyl is unsubstituted or substituted with one or more substituents selected from $R^{13}$,
(6) —$C_{2-4}$alkenyl, where the alkenyl is unsubstituted or substituted with one or more substituents selected from $R^{13}$,
(7) —O$_n$-phenyl or —O$_n$-napthyl, where n is 0 or 1 (wherein if n is 0, a bond is present) and where the phenyl or napthyl is unsubstituted or substituted with one or more substituents selected from $R^{13}$,
(8) —O$_n$-heterocycle, where n is 0 or 1 (wherein if n is 0, a bond is present) and where the heterocycle is unsubstituted or substituted with one or more substituents selected from $R^{13}$,
(9) —(C=O)—NR$^{10}$R$^{11}$,
(10) —NR$^{10}$R$^{11}$,
(11) —S(O)$_2$—NR$^{10}$R$^{11}$,
(12) —NR$^{10}$—S(O)$_2$R$^{11}$,
(13) —S(O)$_q$—R$^{12}$, where q is 0, 1 or 2 and where $R^{12}$ is selected from the definitions of $R^{10}$ and $R^{11}$,
(14) —CO$_2$H,
(15) —CN,
(16) —NO$_2$;
(17) or $R^{5a}$ and $R^{5b}$ taken together form a pyrrolyl or imidazolyl ring, which is unsubstituted or substituted with —CH$_3$, (=CH$_2$), keto, or hydroxyl;

$R^6$ is selected from the group consisting of:
(1) hydrogen,
(2) halogen,
(3) hydroxyl,
(4) —O$_n$—$C_{1-6}$alkyl, where n is 0 or 1 (wherein if n is 0, a bond is present) and where the alkyl is unsubstituted or substituted with one or more substituents selected from $R^{13}$, and
(5) —O$_n$—$C_{3-6}$cycloallyl, where n is 0 or 1 (wherein if n is 0, a bond is present) and where the cycloalkyl is unsubstituted or substituted with one or more substituents selected from $R^{13}$;

$R^{13}$ is selected from the group consisting of:
(1) halogen,
(2) hydroxyl,
(3) —(C=O)$_m$—O$_n$—$C_{1-6}$alkyl, where m is 0 or 1 and n is 0 or 1 (wherein if m is 0 or n is 0, a bond is present, and wherein if m is 0 and n is 0, a single bond is present) where the alkyl is unsubstituted or substituted with one or more substituents selected from $R^{14}$,
(4) —O$_n$—(C$_{1-3}$)perfluoroalkyl,
(5) —(C=O)$_m$—O$_n$—$C_{3-6}$cycloalkyl, where the cycloalkyl is unsubstituted or substituted with one or more substituents selected from $R^{14}$,
(6) —(C=O)$_m$—$C_{2-4}$alkenyl, where the alkenyl is unsubstituted or substituted with one or more substituents selected from $R^{14}$,
(7) —(C=O)$_m$—O$_n$-phenyl or —(C=O)$_m$—O$_n$-napthyl, where the phenyl or napthyl is unsubstituted or substituted with one or more substituents selected from $R^{14}$,
(8) —(C=O)$_m$—O$_n$-heterocycle, where the heterocycle is unsubstituted or substituted with one or more substituents selected from $R^{14}$,
(9) —(C=O)—NR$_{10}$R$^{11}$,
(10) —NR$^{10}$R$^{11}$,
(11) —S(O)$_2$—NR$^{10}$R$^{11}$,

(12) —S(O)$_q$—R$^{12}$,
(13) —CO$_2$H,
(14) —CN, and
(15) —NO$_2$;

R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;

or a pharmaceutically acceptable salt thereof.

An embodiment of the present invention includes compounds of the formula Ia:

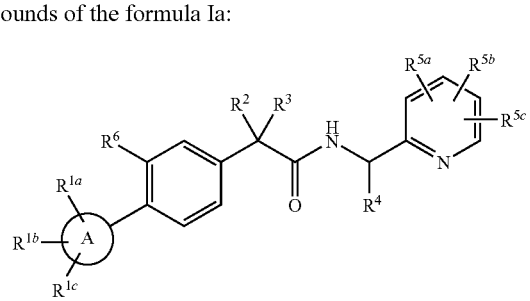

wherein A, R$^{1a}$, R$^{1b}$, R$^{1c}$, R$^2$, R$^3$, R$^4$, R$^{5a}$, R$^{5b}$ and R$^{5c}$ are defined herein; or a pharmaceutically acceptable salt thereof.

An embodiment of the present invention includes compounds of the formula Ia':

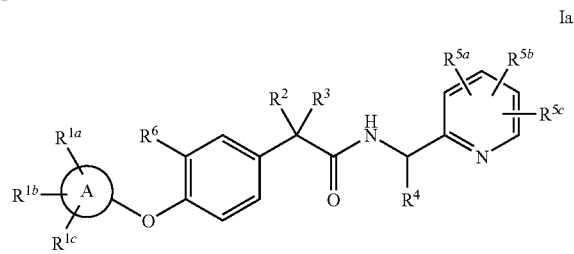

wherein A, R$^{1a}$, R$^{1b}$, R$^{1c}$, R$^2$, R$^3$, R$^4$, R$^{5a}$, R$^{5b}$ and R$^{5c}$ are defined herein; or a pharmaceutically acceptable salt thereof.

An embodiment of the present invention includes compounds of the formula Ib:

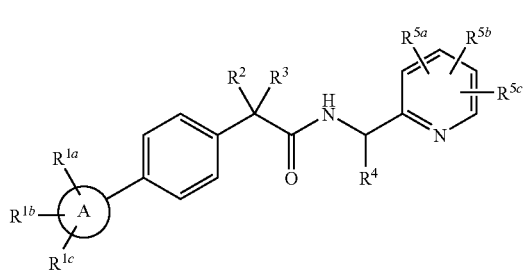

wherein A, R$^{1a}$, R$^{1b}$, R$^{1c}$, R$^2$, R$^3$, R$^4$, R$^{5a}$, R$^{5b}$ and R$^{5c}$ are defined herein; or a pharmaceutically acceptable salt thereof.

An embodiment of the present invention includes compounds of the formula Ic:

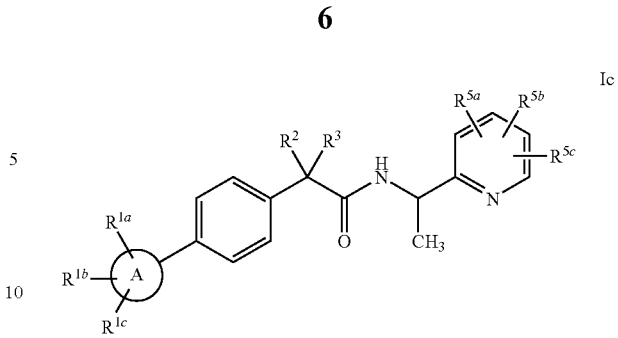

wherein A, R$^{1a}$, R$^{1b}$, R$^{1c}$, R$^2$, R$^3$, R$^{5a}$, R$^{5b}$ and R$^{5c}$ are defined herein; or a pharmaceutically acceptable salt thereof.

An embodiment of the present invention includes compounds of the formula Ic':

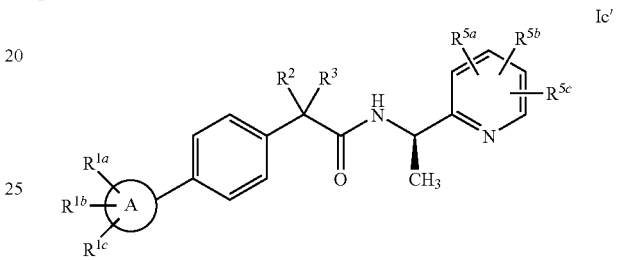

wherein A, R$^{1a}$, R$^{1b}$, R$^{1c}$, R$^2$, R$^3$, R$^{5a}$, R$^{5b}$ and R$^{5c}$ are defined herein; or a pharmaceutically acceptable salt thereof.

An embodiment of the present invention includes compounds of the formula Id:

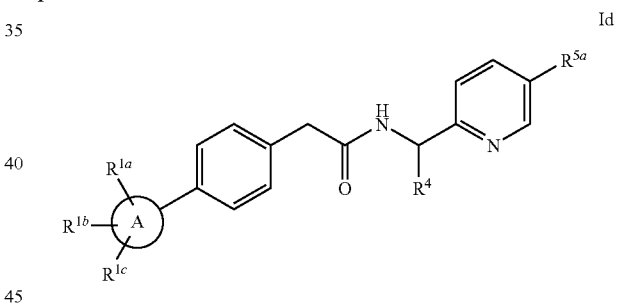

wherein A, R$^{1a}$, R$^4$ and R$^{5a}$ are defined herein; or a pharmaceutically acceptable salt thereof.

An embodiment of the present invention includes compounds of the formula Id':

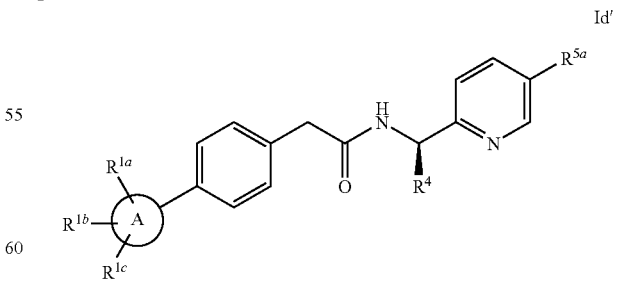

wherein R$^{1a}$, R$^4$ and R$^{5a}$ are defined herein; or a pharmaceutically acceptable salt thereof.

An embodiment of the present invention includes compounds of the formula Id'':

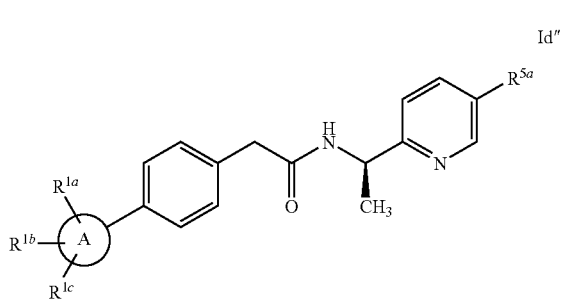

wherein $R^{1a}$ and $R^{5a}$ are defined herein; or a pharmaceutically acceptable salt thereof.

An embodiment of the present invention includes compounds wherein A is selected from the group consisting of:
(1) benzimidazole,
(2) benzofuran;
(3) dihydroisoxazole,
(4) dihydropyrrolopyrrole;
(5) furopyridine,
(6) furopyrrole,
(7) imidazopyrazine,
(8) imidazopyridazine,
(9) imidazopyridine,
(10) imidazopyrimidine,
(11) indazole,
(12) indolizine;
(13) indole,
(14) isoindole,
(15) isoquinoline,
(16) naphthyrindine,
(17) oxotriazolopyridine,
(18) pyrazine,
(19) pyrazolopyrazine,
(20) pyrazolopyridazine,
(21) pyrazolopyrimidine,
(22) pyridazine,
(23) pyridine,
(24) pyridopyrazine,
(25) pyridopyridazine,
(26) pyridopyrimidine,
(27) pyrrolooxazole,
(28) pyrrolopyridine,
(29) pyrrolopyrimidine,
(30) quinazoline,
(31) quinoline,
(32) quinoxaline,
(33) tetrahydrofuran,
(34) thiazole,
(35) triazolopyrazine,
(36) triazolopyridazine,
(37) triazolopyridine, and
(38) triazolopyrimidine.

An embodiment of the present invention includes compounds wherein A is selected from the group consisting of:
(1) 2-benzofuran,
(2) 1,4-dihydropyrrolo[3,2-b]pyrrole,
(3) furo[3,4-b]pyridine,
(4) 4H-furo[3,2-b]pyrrole,
(5) imidazo[1,2-a]pyrazine,
(6) imidazo[1,2-b]pyridazine,
(7) imidazo[1,2-a]pyridine,
(8) imidazo[1,5-a]pyridine,
(9) imidazo[1,2-c]pyrimidine,
(10) indolizine,
(11) 2H-isoindole,
(12) 1,5-naphthyridine,
(13) 1,8-naphthyridine,
(14) pyrazolo[1,5-a]pyrazine,
(15) pyrazolo[1,5-a]pyridine,
(16) pyrazolo[1,5-a]pyrimidine,
(17) pyrazolo[1,5-c]pyrimidine,
(18) pyrido[2,3-b]pyrazine,
(19) pyrido[2,3-c]pyridazine,
(20) pyrido[2,3-d]pyrimidine,
(21) 4H-pyrrolo[2,3-d][1,3]oxazole,
(22) 1H-pyrrolo[2,3-b]pyridine,
(23) 6H-pyrrolo[3,4-b]pyridine,
(24) 7H-pyrrolo[2,3-d]pyrimidine,
(25) quinoxaline,
(26) [1,2,4]triazolo[1,5-a]pyrazine,
(27) [1,2,4]triazolo[1,5-b]pyridazine,
(28) [1,2,3]triazolo[1,5-a]pyridine,
(29) [1,2,4]triazolo[1,5-a]pyridine, and
(30) [1,2,4]triazolo[1,5-c]pyrimidine.

An embodiment of the present invention includes compounds wherein A is selected from the group consisting of:
(1) benzimidazole,
(2) dihydroisoxazole,
(3) imidazopyrazine,
(4) imidazopyridazine,
(5) imidazopyridine,
(6) indazole,
(7) indole,
(8) isoquinoline,
(9) naphthyridine,
(10) pyrazine,
(11) pyrazolopyrazine,
(12) pyrazolopyridazine,
(13) pyrazolopyrimidine,
(14) pyridine,
(15) pyrrolopyridine,
(16) pyrrolopyrimidine,
(17) quinazoline,
(18) quinoxaline,
(19) tetrahydrofuran,
(20) thiazole, and
(21) triazolopyridine.

Within this embodiment, the present invention includes compounds wherein A is selected from the group consisting of:
(1) benzimidazole,
(2) dihydroisoxazole,
(3) indazole,
(4) naphthyridine,
(5) pyrazine,
(6) pyrazolopyrazine,
(7) pyrazolopyridazine,
(8) pyridine,
(9) quinazoline,
(10) tetrahydrofuran, and
(11) thiazole.

Within this embodiment, the present invention includes compounds wherein A is selected from the group consisting of:
(1) 2-cyclopropyl[1,2,4]triazolo[1,5-a]pyridine,
(2) 4,5-dihydroisoxazole,
(3) imidazo[1,2-a]pyrazine,
(4) imidazo[1,2-b]pyridazine,
(5) imidazo[1,2-a]pyridine,
(6) indazole,
(7) isoquinoline, (8) 2-methylimidazo[1,2-b]pyridazine,
(9) 1-methyl-1H-indole,
(10) 1,5-naphthyridine,
(11) pyrazolo[1,5-b]pyridazine,
(12) pyrazolo[1,5-a]pyrimidine,
(13) pyrazolo[1,5-c]pyrimidine,
(14) 1H-pyrrolo[2,3-b]pyridine,
(15) 1H-pyrrolo[3,2-b]pyridine,
(16) 7H-pyrrolo[2,3-d]pyrimidine,
(17) quinazoline,
(18) quinoxaline, and
(19) [1,2,4]triazolo[1,5-a]pyridine.

Within this embodiment, the present invention includes compounds wherein A is benzimidazole. Also within this embodiment, the present invention includes compounds wherein A is indazole. Also within this embodiment, the present invention includes compounds wherein A is dihydroisoxazole. Also within this embodiment, the present invention includes compounds wherein A is isoxazoline (or 4,5-dihydroisoxazole). Also within this embodiment, the present invention includes compounds wherein A is naphthyridine. Also within this embodiment, the present invention includes compounds wherein A is pyrazine. Also within this embodiment, the present invention includes compounds wherein A is pyrazolopyrazine. Also within this embodiment, the present invention includes compounds wherein A is pyrazolopyridazine. Also within this embodiment, the present invention includes compounds wherein A is pyridine. Also within this embodiment, the present invention includes compounds wherein A is quinazoline. Also within this embodiment, the present invention includes compounds wherein A is tetrahydrofuran. Also within this embodiment, the present invention includes compounds wherein A is thiazole.

An embodiment of the present invention includes compounds wherein m is 0. An embodiment of the present invention includes compounds wherein m is 1.

An embodiment of the present invention includes compounds wherein:
$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) phenyl or napthyl, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2$—$R^{10}$, —CN, or —$NR^{10}R^{11}$,
(5) —O-phenyl, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2$—$R^{10}$, —CN, or —$NR^{10}R^{11}$,
(6) $C_{1-6}$alkyl, which is unsubstituted or substituted with halogen, hydroxyl, phenyl or —O—$C_{1-6}$alkyl,
(7) —O—$C_{1-6}$alkyl, which is unsubstituted or substituted with halogen, hydroxyl, phenyl or —O—$C_{1-6}$alkyl,
(8) $C_{3-6}$cycloalkyl, which is unsubstituted or substituted with halogen, hydroxyl or phenyl,
(9) $C_{2-4}$alkenyl, which is unsubstituted or substituted with $C_{3-6}$cycloalkyl or phenyl,
(10) heterocycle, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2H$, —CN, or —$NR^{10}R^{11}$,
(11) —$NR^{10}R^{11}$, wherein $R^{10}$ and $R^{11}$ are independently selected from hydrogen and $C_{1-6}$alkyl,
(12) —$S(O)_2$—$NR^{10}R^{11}$,
(13) —$S(O)_q$—$R^{12}$, where q is 0, 1 or 2 and where $R^{12}$ is $C_{1-6}$alkyl, $C_{3-6}$cycloalkyl, or phenyl which is unsubstituted or substituted with halogen, hydroxyl, phenyl or —O—$C_{1-6}$allyl,
(14) —$CO_2H$,
(15) —$CO_2$—$R^{12}$, and
(16) —CN,
or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

An embodiment of the present invention includes compounds wherein $R^{1a}$, $R^{1b}$ and $R^{1c}$ are independently selected from the group consisting of:
(1) hydrogen,
(2) halogen,
(3) phenyl or napthyl, which is unsubstituted or substituted with halogen, hydroxyl, $C_{1-6}$alkyl, —O—$C_{1-6}$alkyl, $C_{3-6}$cycloalkyl, —SH, —S—$C_{1-6}$alkyl, —$NO_2$, —$CO_2H$, or —CN,
(4) —O-phenyl, which is unsubstituted or substituted with halogen, hydroxyl, $C_{1-6}$alkyl, —O—$C_{1-6}$alkyl, —SH, —S—$C_{1-6}$alkyl, —SH, —$NO_2$, —$CO_2H$, or —CN,
(5) $C_{1-6}$alkyl, which is unsubstituted or substituted with halogen, hydroxyl, phenyl or —O—$C_{1-6}$alkyl,
(6) $C_{3-6}$cycloallyl, which is unsubstituted or substituted with halogen, hydroxyl, phenyl or —O—$C_{1-6}$alkyl,
(7) $C_{2-4}$alkenyl, which is unsubstituted or substituted with $C_{3-6}$cycloalkyl or phenyl,
(8) —$NR^{10}R^{11}$, wherein $R^{10}$ and $R^{11}$ are independently selected from hydrogen and $C_{1-6}$alkyl,
(9) isoxazolyl, which is unsubstituted or substituted with $C_{1-6}$alkyl,
(10) imidazolyl, which is unsubstituted or substituted with $C_{1-6}$alkyl,
(11) morpholinyl, which is unsubstituted or substituted with $C_{1-6}$alkyl,
(12) oxazolyl, which is unsubstituted or substituted with $C_{1-6}$alkyl,
(13) pyrazolyl, which is unsubstituted or substituted with $C_{1-6}$alkyl,
(14) pyrrolidinyl, which is unsubstituted or substituted with halogen,
(15) tetrazolyl, which is unsubstituted or substituted with $C_{1-6}$alkyl,
(16) thienyl, which is unsubstituted or substituted with $C_{1-6}$alkyl,
(17) benzothienyl, which is unsubstituted or substituted with $C_{1-6}$alkyl,
(18) thiophenyl, which is unsubstituted or substituted with $C_{1-6}$alkyl,
(19) triazolyl, which is unsubstituted or substituted with $C_{1-6}$alkyl,
(20) —$NO_2$, and
(21) —CN,
or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

Within this embodiment, the present invention includes compounds wherein $R^{1c}$ is hydrogen, and $R^{1a}$ and $R^{1b}$ are selected from the group consisting of:
(1) halogen,
(2) phenyl or napthyl, which is unsubstituted or substituted with halogen, hydroxyl, $C_{1-6}$alkyl, —O—$C_{1-6}$alkyl, $C_{3-6}$cycloalkyl, —SH, —S—$C_{1-6}$alkyl, —$NO_2$, —$CO_2$—$C_{1-6}$alkyl, or —CN, (3) —O-phenyl, which is unsubstituted or substituted with halogen, hydroxyl, $C_{1-6}$alkyl, —O—$C_{1-6}$alkyl, —SH, —S—$C_{1-6}$alkyl, —$NO_2$, —$CO_2$—$C_{1-6}$alkyl, or —CN,
(4) $C_{1-6}$alkyl, which is unsubstituted or substituted with halogen, hydroxyl, phenyl or —O—$C_{1-6}$alkyl,
(5) $C_{3-6}$cycloallyl, which is unsubstituted or substituted with halogen, hydroxyl, phenyl or —O—$C_{1-6}$alkyl,
(6) $C_{2-4}$alkenyl, which is unsubstituted or substituted with $C_{3-6}$cycloalkyl or phenyl,
(7) —$NR^{10}R^{11}$, wherein $R^{10}$ and $R^{11}$ are independently selected from hydrogen and $C_{1-6}$alkyl,
(8) isoxazolyl, which is unsubstituted or substituted with $C_{1-6}$alkyl,
(9) imidazolyl, which is unsubstituted or substituted with $C_{1-6}$alkyl,
(10) morpholinyl, which is unsubstituted or substituted with $C_{1-6}$alkyl,
(11) oxazolyl, which is unsubstituted or substituted with $C_{1-6}$alkyl,
(12) pyrazolyl, which is unsubstituted or substituted with $C_{1-6}$alkyl,
(13) pyrrolidinyl, which is unsubstituted or substituted with halogen,
(14) tetrazolyl, which is unsubstituted or substituted with $C_{1-6}$alkyl,
(15) thienyl, which is unsubstituted or substituted with $C_{1-6}$alkyl,
(16) benzothienyl, which is unsubstituted or substituted with $C_{1-6}$alkyl,
(17) thiophenyl, which is unsubstituted or substituted with $C_{1-6}$alkyl, and
(18) triazolyl, which is unsubstituted or substituted with $C_{1-6}$alkyl,
or $R^{1a}$ and $R^{1b}$ taken together form a cyclopentyl, cyclohexyl, dihydrofuranyl or dihydropyranyl ring, which is unsubstituted or substituted with —$CH_3$, (=$CH_2$), keto, or hydroxyl.

Within this embodiment, the present invention includes compounds wherein $R^{1b}$ is hydrogen, $R^{1c}$ is hydrogen and $R^{1a}$ is independently selected from the group consisting of:
(1) halogen,
(2) phenyl, which is unsubstituted or substituted with halogen, hydroxyl, $C_{1-6}$alkyl, —O—$C_{1-6}$alkyl, $C_{3-6}$cycloalkyl, or —$NO_2$,
(3) —O-phenyl, which is unsubstituted or substituted with halogen, hydroxyl, $C_{1-6}$alkyl or —O—$C_{1-6}$alkyl,
(4) $C_{1-6}$alkyl, which is unsubstituted or substituted with halogen, hydroxyl or phenyl,
(5) $C_{3-6}$cycloalkyl, which is unsubstituted or substituted with halogen, hydroxyl or phenyl, and
(6) $C_{2-4}$alkenyl, which is unsubstituted or substituted with $C_{3-6}$cycloalkyl or phenyl.

Within this embodiment, the present invention includes compounds wherein $R^{1a}$ is $C_{1-6}$alkyl, which is unsubstituted or substituted with halogen, $R^{1b}$ is hydrogen and $R^{1c}$ is hydrogen.

Within this embodiment, the present invention includes compounds wherein $R^{1a}$ is $C_{3-6}$cycloalkyl, $R^{1b}$ is hydrogen and $R^{1c}$ is hydrogen.

Within this embodiment, the present invention includes compounds wherein $R^{1a}$ is halogen, $R^{1b}$ is hydrogen and $R^{1c}$ is hydrogen.

Within this embodiment, the present invention includes compounds wherein $R^{1a}$ is $C_{1-6}$alkyl, $R^{1b}$ is hydrogen and $R^{1c}$ is hydrogen.

Within this embodiment, the present invention includes compounds wherein $R^{1a}$ is isopropyl or tert-butyl, $R^{1b}$ is hydrogen and $R^{1c}$ is hydrogen.

Within this embodiment, the present invention includes compounds wherein $R^{1a}$ is hydrogen, $R^{1b}$ is hydrogen and $R^{1c}$ is hydrogen.

An embodiment of the present invention includes compounds wherein $R^2$ and $R^3$ are independently selected from the group consisting of:
(1) hydrogen;
(2) halogen,
(3) $C_{1-6}$alkyl, which is unsubstituted or substituted with halo, $C_{3-6}$cycloalkyl or phenyl, and
(4) $C_{3-6}$cycloalkyl, which is unsubstituted or substituted with halo, $C_{3-6}$cycloalkyl or phenyl.

Within this embodiment, the present invention includes compounds wherein $R^2$ and $R^3$ are independently selected from the group consisting of:
(1) hydrogen,
(2) fluoro,
(3) $C_{1-6}$alkyl, which is unsubstituted or substituted with halogen or $C_{3-6}$cycloalkyl, and
(4) $C_{3-6}$cycloallyl.

Within this embodiment, the present invention includes compounds wherein $R^2$ is hydrogen and $R^3$ is hydrogen. Within this embodiment, the present invention includes compounds wherein $R^2$ is fluoro and $R^3$ is fluoro. Within this embodiment, the present invention includes compounds wherein $R^2$ is methyl and $R^3$ is hydrogen. Within this embodiment, the present invention includes compounds wherein $R^2$ is cyclopropyl and $R^3$ is hydrogen.

An embodiment of the present invention includes compounds wherein $R^4$ is other than hydrogen.

Within this embodiment, the present invention includes compounds wherein $R^4$ is in the (R) orientation.

An embodiment of the present invention includes compounds wherein $R^4$ is selected from the group consisting of:
(1) $C_{1-6}$alkyl, which is unsubstituted or substituted with halogen, hydroxyl, —O—$C_{1-6}$alkyl, $C_{3-6}$cycloalkyl, phenyl, or —$NR^{10}R^{11}$, wherein $R^{10}$ and $R^{11}$ are independently selected from the group consisting of hydrogen, and $C_{1-6}$alkyl, which is unsubstituted or substituted with halogen, hydroxyl or phenyl,
(2) —$C_{3-6}$cycloalkyl, which is unsubstituted or substituted with halogen, $C_{1-6}$alkyl or phenyl,
(3) —$C_{2-6}$alkenyl,
(4) phenyl, which is unsubstituted or substituted with halogen, hydroxyl, $C_{1-6}$alkyl, —O—$C_{1-6}$alkyl or —$NO_2$,
(5) —(C=O)—$NR^{10}R^{11}$, and
(6) —(C=O)—O—$C_{1-6}$alkyl, which is unsubstituted or substituted with halogen, $C_{3-6}$cycloalkyl or phenyl.

An embodiment of the present invention includes compounds wherein $R^4$ is selected from the group consisting of:
(1) $C_{1-6}$alkyl, which is unsubstituted or substituted with halogen, hydroxyl, or —O—$C_{1-6}$alkyl, and
(2) —$C_{2-6}$alkenyl,
(3) —$C_{3-6}$cycloalkyl.

Within this embodiment, the present invention includes compounds wherein $R^4$ is selected from the group consisting of:
(1) $CH_3$,
(2) $CH_2OH$,
(3) $CH_2OCH_3$,
(4) $CH_2CH_3$,
(5) $CH=CH_2$,
(6) $CH_2CH_2OH$,
(7) $CH_2CH=CH_2$, (8) CH$_2$CH$_2$F,
(9) CH$_2$CF$_2$,
(10) CH$_2$-phenyl,
(12) CH$_2$-cyclopropyl,
(13) CH$_2$-cyclobutyl,
(14) cyclopropyl,
(15) cyclobutyl,
(16) CH$_2$CH$_2$CH$_3$, and
(17) —(C=O)—O—CH$_3$.

Within this embodiment, the present invention includes compounds wherein R$^4$ is CH$_3$, CH$_2$CH$_3$, CH$_2$OH, CH$_2$CH$_2$OH or cyclopropyl.

Within this embodiment, the present invention includes compounds wherein R$^4$ is CH$_3$.

Within this embodiment, the present invention includes compounds wherein R$^4$ is (R) —CH$_3$.

An embodiment of the present invention includes compounds wherein R$^{5a}$, R$^{5b}$ and R$^{5c}$ are independently selected from the group consisting of:
(1) hydrogen,
(2) halogen,
(3) hydroxyl,
(4) C$_{1-6}$alkyl, which is unsubstituted or substituted with halogen, hydroxyl, phenyl, —O—C$_{1-6}$alkyl, —O—(CO)C$_{1-6}$alkyl, or C$_{3-6}$cycloallyl, and
(5) —C$_{2-4}$alkenyl.

An embodiment of the present invention includes compounds wherein R$^{5a}$, R$^{5b}$ and R$^{5c}$ are independently selected from the group consisting of:
(1) hydrogen,
(2) —O—C$_{1-6}$alkyl, which is unsubstituted or substituted with halogen, hydroxyl, phenyl, —O—C$_{1-6}$alkyl, or C$_{3-6}$cycloalkyl,
(3) C$_{3-6}$cycloalkyl, which is unsubstituted or substituted with halogen, hydroxyl or phenyl,
(4) —NH—C$_{1-6}$alkyl, which is unsubstituted or substituted with halogen, hydroxyl, phenyl, —O—C$_{1-6}$alkyl, —O—(CO)C$_{1-6}$alkyl, or C$_{3-6}$cycloalkyl,
(5) —N(C$_{1-6}$alkyl)$_2$, which each alkyl independently is unsubstituted or substituted with halogen, hydroxyl, phenyl, —O—C$_{1-6}$alkyl, —O—(CO)C$_{1-6}$alkyl, or C$_{3-6}$cycloalkyl,
(6) phenyl, which is unsubstituted or substituted with halogen, hydroxyl, C$_{1-6}$alkyl, —O—C$_{1-6}$alkyl or —NO$_2$,
(7) —O-phenyl, which is unsubstituted or substituted with halogen, hydroxyl, C 6alkyl, —O—C$_{1-6}$alkyl or —NO$_2$,
(8) —S(O)$_2$—NH—C$_{1-6}$alkyl,
(9) —S(O)$_2$—N(C$_{1-6}$alkyl)$_2$, and
(10) —S(O)$_2$—C$_{1-6}$alkyl.

An embodiment of the present invention includes compounds wherein R$^{5a}$, R$^{5b}$ and R$^{5c}$ are independently selected from the group consisting of:
(1) hydrogen,
(2) heterocycle, which is unsubstituted or substituted with halogen, hydroxyl, keto, C$_{1-6}$alkyl or —O—C$_{1-6}$alkyl,
(3) —O-heterocycle, which is unsubstituted or substituted with halogen, hydroxyl, keto, C$_{1-6}$alkyl or —O—C$_{1-6}$alkyl, and
(4) —NH-heterocycle, which is unsubstituted or substituted with halogen, hydroxyl, keto, C$_{1-6}$ alkyl or —O—C$_{1-6}$alkyl.

An embodiment of the present invention includes compounds wherein R$^{5b}$ is hydrogen, R$^{5c}$ is hydrogen and R$^{5a}$ is independently selected from the group consisting of:
(1) hydrogen,
(2) fluoro,
(3) chloro,
(4) bromo,
(5) hydroxyl,
(6) —CH$_3$,
(7) —CH$_2$OH,
(8) —CH$_2$CH$_3$,
(9) —CH$_2$=CH$_2$,
(10) —CH$_2$CH$_2$CH$_3$, and
(11) -cyclopropyl.

Within this embodiment, the present invention includes compounds wherein R$^{5b}$ is hydrogen, R$^{5c}$ is hydrogen and R$^{5a}$ is —O—C$_{1-6}$alkyl, which is unsubstituted or substituted with halogen, hydroxyl, phenyl, —O—C$_{1-6}$alkyl, or C$_{3-6}$cycloalkyl.

An embodiment of the present invention includes compounds wherein R$^{5b}$ is hydrogen, R$^{5c}$ is hydrogen and R$^{5a}$ is independently selected from the group consisting of:
(1) hydrogen,
(2) —OCH$_3$,
(3) —OCH$_2$F,
(4) —OCH$_2$-cyclopropyl,
(5) —OCH$_2$-phenyl,
(6) —OCH$_2$CH$_3$,
(7) —OCH$_2$CF$_3$,
(8) —OCH$_2$CH$_2$CH$_3$,
(9) —OCH$_2$(C=O)OCH$_2$CH$_3$,
(10) —OCH$_2$(C=O)NHCH$_2$CH$_3$,
(11) —OSO$_2$CH$_3$, and
(12) —O(C=O)OCH$_3$.

Within this embodiment, the present invention includes compounds wherein R$^{5b}$ is hydrogen, R$^{5c}$ is hydrogen and R$^{5a}$ is —OCH$_2$CF$_3$.

An embodiment of the present invention includes compounds wherein R$^{5b}$ is hydrogen, R$^{5c}$ is hydrogen and R$^{5a}$ is independently selected from the group consisting of:
(1) hydrogen,
(2) —NHCH$_2$CF$_3$,
(3) —NHCH$_2$C(CH$_3$)$_3$,
(4) —NHCH$_2$CH$_2$C(CH$_3$)$_3$,
(5) —NHCH(CH$_3$)CH$_2$CH$_3$,
(6) —NH-cyclopropyl, and
(7) —NHCH$_2$-cyclopropyl.

An embodiment of the present invention includes compounds wherein R$^{5b}$ is hydrogen, R$^{5c}$ is hydrogen and R$^{5a}$ is independently selected from the group consisting of:
(1) hydrogen,
(2) pyridyl,
(3) —O-pyridyl,
(4) —NH-pyridyl,
(5) imidazolyl,
(6) oxazolyl,
(7) pyrrolyl,
(8) pyrrolidinyl, which is unsubstituted or substituted with C$_{1-6}$alkyl, keto or halo,
(9) morpholinyl, which is unsubstituted or substituted with C$_{1-6}$ alkyl,
(10) thiomorpholinyl, which is unsubstituted or substituted with C$_{1-6}$alkyl, and
(11) piperazinyl, which is unsubstituted or substituted with C$_{1-6}$alkyl.

Within this embodiment, the present invention includes compounds wherein R$^{5b}$ is hydrogen and R$^{5c}$ is hydrogen.

Within this embodiment, the present invention includes compounds wherein R$^{5a}$ is located at the 5-position of the pyridyl, R$^{5b}$ is hydrogen and R$^{5c}$ is hydrogen.

An embodiment of the present invention includes compounds wherein R$^6$ is selected from the group consisting of:

(1) hydrogen,
(2) halogen,
(3) hydroxyl,
(4) —$O_n$—$C_{1-6}$alkyl, where n is 0 or 1 (wherein if n is 0, a bond is present) and where the alkyl is unsubstituted or substituted with one or more substituents selected from halogen, hydroxyl, phenyl, —O—$C_{1-6}$alkyl, —O—(CO)$C_{1-6}$alkyl, or $C_{3-6}$cycloalkyl, and
(5) —$O_n$—$C_{3-6}$cycloalkyl, where n is 0 or 1 (wherein if n is 0, a bond is present) and where the cycloalkyl is unsubstituted or substituted with one or more substituents selected from halogen, hydroxyl, phenyl, —O—$C_{1-6}$alkyl, —O—(CO)$C_{1-6}$alkyl, or $C_{3-6}$cycloalkyl.

Within this embodiment, the present invention includes compounds wherein $R^6$ is selected from the group consisting of:
(1) hydrogen,
(2) halogen,
(3) hydroxyl, and
(4) —$C_{1-6}$alkyl, and where the alkyl is unsubstituted or substituted with one or more substituents selected from halogen, hydroxyl, phenyl, —O—$C_{1-6}$alkyl, —O—$C_{1-6}$alkyl, —O—(CO) $C_{1-6}$alkyl, or $C_{3-6}$cycloalkyl.

Within this embodiment, the present invention includes compounds wherein $R^6$ is selected from the group consisting of:
(1) hydrogen,
(2) halogen,
(3) hydroxyl, and
(4) —$C_{1-6}$alkyl.

Within this embodiment, the present invention includes compounds wherein $R^6$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. Similarly, $C_{2-6}$alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, dihydroisoxazole, furanyl, imidazolyl, imidazopyridazine, imidazopyrazine, indolinyl, indolyl, indolizinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridazinyl, pyridopyrimidinyl, pyridopyrazinyl, pyridazinyl, pyridyl, pyrimidinyl, pyrazolyl, pyrazolopyridazinyl, pyrazolopyridinyl, pyrazolopyrimidinyl, pyrrolyl, pyrrolopyridazinyl, pyrrolopyridinyl, pyrrolopyrimidinyl, quinazolinyl, quinolyl, quinoxalinyl, tetrazolyl, tetrazolopyridyl, thiadiazolyl, thiazolyl, thienyl, triazolopyridazinyl, triazolopyridinyl, triazolopyrimidinyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing T-type calcium channel activity in a patient such as a mammal in need of such inhibition comprising the administration of an effective amount of the compound. The present invention is directed to the use of the compounds disclosed herein as antagonists of T-type calcium channels activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing T-type calcium channel activity or treating the disorders and diseases noted herein in humans and animals.

The subject treated in the present methods is generally a mammal, in particular, a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as T-type calcium channel antagonists may be readily determined without undue experimentation by methodology well known in the art, including the "FLIPR $Ca^{2+}$ Flux Assay" and the "T-type Calcium ($Ca^{2+}$) Antagonist Voltage-Clamp Assay" [described by Xia, et al., Assay and Drug Development Tech., 1(5), 637-645 (2003)]. In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. Nos. 5,618,720, 5,686,241, 5,710,250,5,726,035, 5,792,846, 5,846,757, 5,851,824, 5,874,236, 5,876,958, 6,013,474, 6,057,114, 6,096,514, WO 99/28342, and J. Neuroscience, 19(6):1912-1921 (1999). Cells expressing the T-type channels were grown in growth media which comprised: DMEM, 10% Tet-system approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 20 mM HEPES, 30 Glucose, pH 7.4. The internal solution consists of (mM): 125 CsCl, 10 TEA-Cl, 10 HEPES, 8 NaCl, 0.06 CaCl2, 0.6 EGTA, 4 ATP-Mg, 0.3 GTP; 135 mM CsMeSO3, 1 MgCl2, 10 CsCl, 5 EGTA, 10 HEPES, pH 7.4; or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1)-80 mV holding potential every 20 seconds pulse to -20 mV for 70 msec duration; the effectiveness of the drug in inhibiting the current mediated by the channel is measured directly from measuring the reduction in peak current amplitude initiated by the voltage shift from -80 mV to -20 mV; (2). -100 mV holding potential every 15 seconds pulse to -20 mV for 70 msec duration; the effectiveness of the drug in inhibiting the current mediated by the channel is measured directly from measuring the reduction in peak current amplitude initiated by the shift in potential from -100 mV to -20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays. In particular, the compounds of the following examples had activity in antagonizing the T-type calcium channel in the aforementioned assays, generally with an $IC_{50}$ of less than about 10 μM. Some of the compounds within the present invention had activity in antagonizing the T-type calcium channel in the aforementioned assays with an $IC_{50}$ of less than about 1 μM. Such a result is indicative of the intrinsic activity of the compounds in use as antagonists of T-type calcium channel activity.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions. For example, with respect to compounds disclosed in PCT Application WO 2007/120729 (published Oct. 25, 2007), the present compounds exhibit unexpected properties, such as having a shorter duration of action (e.g. half-life, t ½).

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; overactive bladder (OAB); urge urinary incontinence (UUI); lower urinary tract symptoms (LUTS); substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, diabetic neuropathy, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in an embodiment the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention. The subject compounds are further useful in a method for the prevention, treatment, control, amelioration, or reducation of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of T-type calcium channel. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine. In another embodiment, the subject compound may be employed in combination with an NK-1 receptor antagonists, a beta-3 agonist, a 5-alpha reductase inhibitor (such as finasteride or dutasteride), a M3 muscarinic receptor antagonist (such as darifenacin, fesoterodine, oxybutynin, solifenacin, tolterodine or trosipium) or duloxetine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth-hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et$_3$N: triethylamine; DCM: dichloromethane; DCE: dichloroethane; DME: dimethoxyethane; DEA: diethylamine; DAST: diethylaminosulfur trifluoride; EtMgBr: ethylamgnesium bromide; BSA: bovine serum albumin; TFA: trifluoroacetic acid; DMF: N,N-dimethylformamide; SOCl$_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME 1

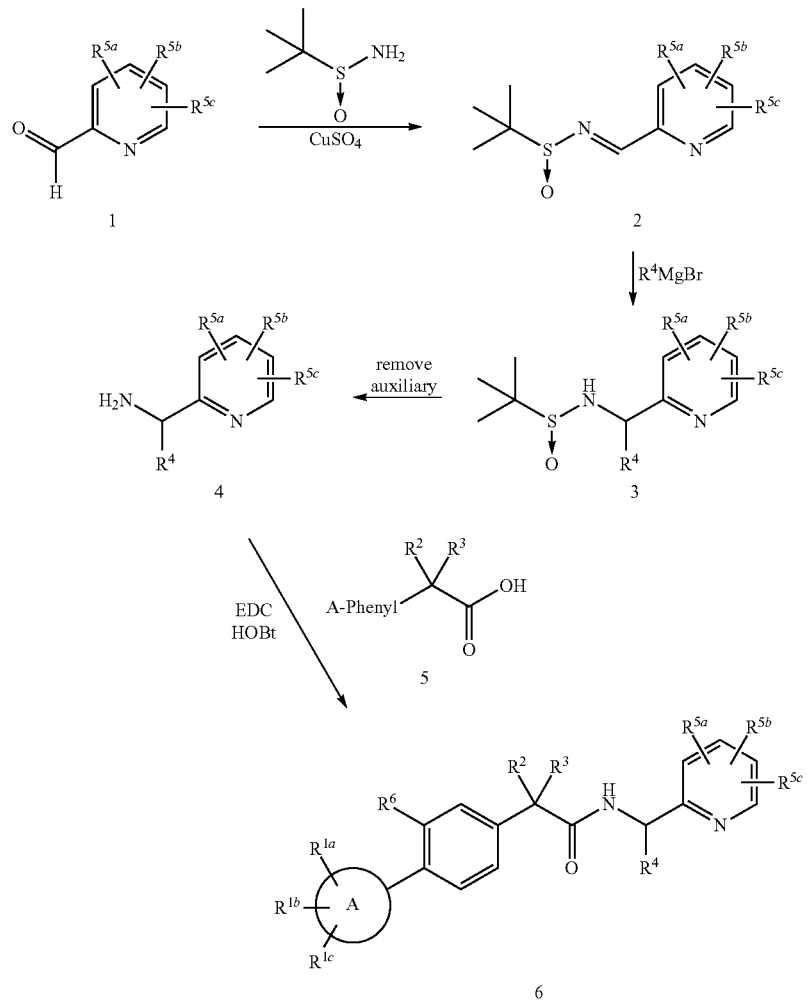

Compounds of the invention may be prepared as outlined in Scheme 1. An appropriately substituted 2-formylpyridine 1 is condensed with tert-butane sulfinamide and addition of an organometallic reagent introduces the R$^4$ substituent. Removal of the auxiliary provides amines 4 which can be coupled to a variety of carboxylic acid derivatives 5 to afford compounds of the formula 6. Compound of the formula 6 can be further modified by manipulation of the substituent groups by general methods known in the art, including (but not limited to) cross coupling, oxidation, reduction, dealkylation, alkylation, acylation and the like.

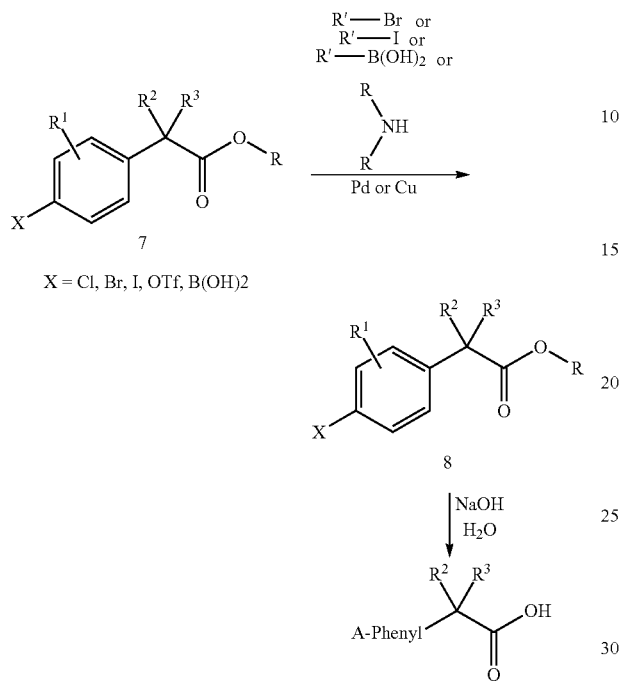

SCHEME 2

X = Cl, Br, I, OTf, B(OH)2

Intermediate carboxylic acid derivatives of formula 5 may be prepared as shown in Scheme 2. Thermal or metal mediated (e.g. palladium or copper) coupling of appropriately substituted halides, amines, and boronic acids with appropriately substituted esters 7 give esters of the formula 8 which can be hydrolyzed to the desired acids 5.

INTERMEDIATE 1

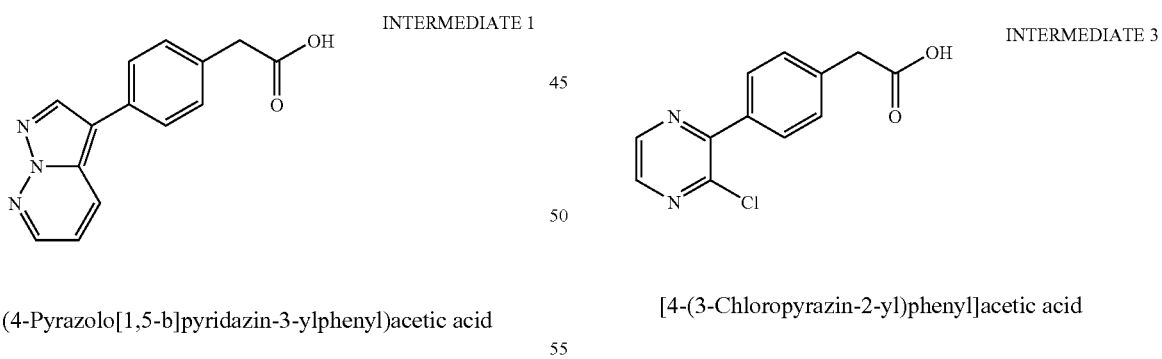

(4-Pyrazolo[1,5-b]pyridazin-3-ylphenyl)acetic acid

To a solution of 1.00 g (3.82 mmol) [4-(4,4,5,5-tetramethyl-1,3,2-dioxaborolan-2-yl)phenyl]acetic acid in 5.70 ml CH$_3$CN and 3.80 ml water was added 0.76 g (3.82 mmol) 3-bromopyrazolo[1,5-b]pyridazine, 8.57 mg (0.038 mmol) palladium acetate, 1.21 g (8.77 mmol) potassium carbonate, and 0.031 g (0.076 mmol) SPhos. The resulting suspension was degassed for 5 minutes. After 30 min in the microwave at 150° C., the reaction mixture was cooled, acidified with 1N HCl, extracted with ethyl acetate, and washed with brine. The organic layer was dried over Na$_2$SO$_4$, filtered and concentrated in vacuo. Purification by flash chromatography (silica gel, linear gradient 50-100% EtOAc in hexanes) afforded 0.69 g (72%) (4-pyrazolo[1,5-b]pyridazin-3-ylphenyl)acetic acid. $^1$H NMR (CD$_3$OD, 400 MHz) 8.40 (dd, J=1.83, 15.75 Hz, 1H); 8.40 (m, 1H); 8.28 (s, 1H); 7.62 (d, J=8.05 Hz, 2H); 7.41 (d, J=7.97 Hz, 2H); 7.22 (dd, J=4.4, 9.1 Hz, 1H); 3.66 (s, 2H). ES-MS M+1=254.1.

INTERMEDIATE 2

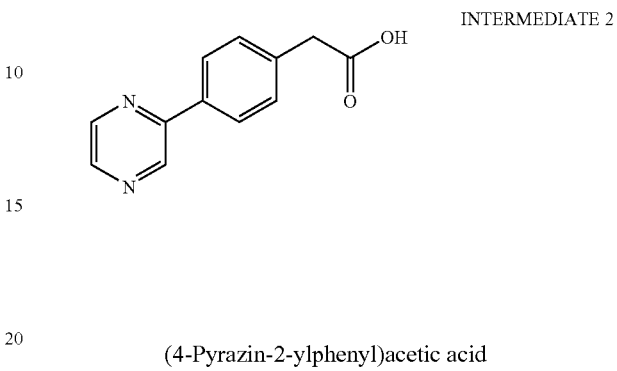

(4-Pyrazin-2-ylphenyl)acetic acid

To a solution of 0.40 g (1.53 mmol) of [4-(4,4,5,5-tetramethyl-1,3,2-dioxaborolan-2-yl)phenyl]acetic acid in 4.0 ml of dioxane was added 0.18 mL (1.73 mmol) of 2-iodopyrazine, 10.3 mg (0.037 mmol) of tricyclohexylphosphine, 13.9 mg (0.015 mmol) of Pd$_2$(dba)$_3$, and 2.0 ml (1.27 M, 2.59 mmol) of aqueous potassium phosphate solution. The resulting suspension was degassed for 10 mins. After 30 min in the microwave at 150° C., the reaction mixture was cooled, acidified with 1N HCl, extracted with ethyl acetate, and washed with brine. The organic layer was dried over Na$_2$SO$_4$, filtered and concentrated in vacuo. Purification by preparative HPLC (5->95% CH$_3$CN/H$_2$O over 15 min, 0.05% added TFA, C18) afforded 0.10 g (32%) of (4-pyrazin-2-ylphenyl)acetic acid. $^1$H NMR (CD$_3$OD, 400 MHz) 9.1 (s, 1H); 8.66 (t, J=1.74 Hz, 1H); 8.51 (d, J=2.57 Hz, 1H); 8.04 (d, J=8.15 Hz, 2H); 7.46 (d, J=8.15 Hz, 2H); 3.70 (s, 2H). ES-MS M+1=215.1.

INTERMEDIATE 3

[4-(3-Chloropyrazin-2-yl)phenyl]acetic acid

To a solution of 0.10 g (0.38 mmol) [4-(4,4,5,5-tetramethyl-1,3,2-dioxaborolan-2-yl)phenyl]acetic acid in 1.2 ml of dioxane was added 0.17 g (1.15 mmol) of 2,3-dichloropyrazine, 2.57 mg (0.009 mmol) of tricyclohexylphosphine, 3.5 mg (0.004 mmol) of Pd$_2$(dba)$_3$, and 0.51 ml (1.27 M, 0.65 mmol) of aqueous potassium phosphate solution. The resulting suspension was degassed for 10 minutes. After 30 min in the microwave at 100° C., the reaction mixture was cooled, acidified with 1N HCl, extracted with ethyl acetate, and washed with brine. The organic layer was dried over Na$_2$SO$_4$, filtered and concentrated in vacuo to afford crude [4-(3-chloropyrazin-2-yl)phenyl]acetic acid. ES-MS M+1=249.1.

INTERMEDIATE 4

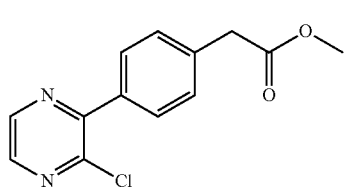

Methyl [4-(3-chloropyrazin-2-yl)phenyl]acetate

To a solution of 0.40 g (1.6 mmol) of [4-(3-chloropyrazin-2-yl)phenyl]acetic acid in 3.0 mL of DMF was added 0.67 g (4.8 mmol) of potassium carbonate and 0.14 mL (2.3 mmol) iodomethane. After 1 h at 40° C., the reaction mixture was cooled, diluted with CH$_2$Cl$_2$, washed three times with water followed by brine. The organic layer was dried over Na$_2$SO$_4$, filtered and concentrated in vacuo. Purification by flash chromatography (silica gel, linear gradient 0-75% EtOAc in hexanes) afforded 0.15 g (36%) methyl [4-(3-chloropyrazin-2-yl)phenyl]acetate. ES-MS M+1=263.0.

INTERMEDIATE 5

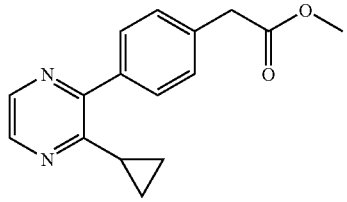

Methyl [4-(3-cyclopropylpyrazin-2-yl)phenyl]acetate

To a solution of 0.15 g (0.57 mmol) of methyl [4-(3-chloropyrazin-2-yl)phenyl]acetate acid in 3.0 mL of toluene and 0.15 mL of water were added 63.8 mg (0.74 mmol) of cyclopropyl boronic acid, 16 mg (0.06 mmol) of tricyclohexylphosphine, 7.8 mg (0.009 mmol) of Pd$_2$(dba)$_3$, and 0.42 g (2.0 mmol) of potassium phosphate. The resulting suspension was degassed for 10 minutes. After 1 h in the microwave at 140° C., the reaction mixture was cooled, diluted with CH$_2$Cl$_2$, wash three times with water, and washed with brine. The organic layer was dried over Na$_2$SO$_4$, filtered and concentrated in vacuo. Purification by flash chromatography (silica gel, linear gradient 0-40% EtOAc in hexanes) afforded 0.10 g (65%) methyl [4-(3-cyclopropylpyrazin-2-yl)phenyl]acetate. $^1$H NMR (CDCl$_3$, 400 MHz) δ 8.35 (m, 2H); 7.68 (d, J=8.06 Hz, 2H); 7.41 (d, J=8.06 Hz, 2H); 3.72 (s, 3H); 3.71 (s, 2H); 2.22 (m, 1H); 1.19 (m, 2H); 0.99 (m, 2H). ES-MS M+1=269.1.

INTERMEDIATE 6

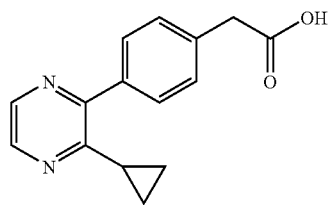

[4-(3-Cyclopropylpyrazin-2-yl)phenyl]acetic acid

To a solution of 0.10 g (0.37 mmol) of methyl [4-(3-cyclopropylpyrazin-2-yl)phenyl]acetate in 0.75 ml of MeOH was added 0.75 mL (0.75 mmol) of 1N LiOH. After 1 h at room temperature, the reaction mixture was acidified with 1 N HCl, extracted twice with ethyl acetate. The combined organic layers were washed with brine. The organic layer was dried over Na$_2$SO$_4$, filtered and concentrated in vacuo to afforded 0.080 g (84%) of [4-(3-cyclopropylpyrazin-2-yl)phenyl]acetic acid. ES-MS M+1=255.1.

Example 1

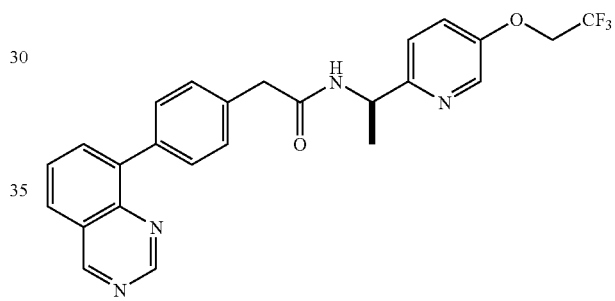

2-(4-Quinazolin-8-ylphenyl)-N-{(1R)-1-[5-(2,2,2-trifluoroethoxy)pyridin-2-yl]ethyl}acetamide To a suspension of (R)-1-[5-(2,2,2-trifluoroethoxy)pyridin-2-yl]ethylamine bis-HCl (0.75 g, 2.6 mmol), 4-(4,4,5,5-tetramethyl-1,3,2-dioxaborolan-2-yl)phenylacetic acid (0.67 g, 2.6 mmol), EDC (0.59 g, 3.1 mmol), and 1-hydroxy-7-azabenzotriazole (0.42 g, 3.1 mmol) in DMF (5 mL) was added diisopropylethylamine (1.8 mL, 10.2 mmol). After stirring for 90 min at room temperature, the reaction mixture was loaded directly onto a silica gel column and purified by normal phase chromatography (20-80% EtOAc/hexanes) to give 2-[4-(4,4,5,5-tetramethyl-1,3,2-dioxaborolan-2-yl)phenyl)]-N-{(1R)-1-[5-(2,2,2-trifluoroethoxy)pyridin-2-yl]ethyl}acetamide (0.77 g, 65%) as a viscous oil that slowly solidified to a white solid. MS (Electrospray): m/z 465.1 (M$^+$H). To a microwave vial containing 2-[4-(4,4,5,5-tetramethyl-1,3,2-dioxaborolan-2-yl)phenyl)]-N-{(1R)-1-[5-(2,2,2-trifluoroethoxy)pyridin-2-yl]ethyl}acetamide (50 mg, 0.11 mmol), 8-bromoquinazoline (25 mg, 0.12 mmol), and bis(triphenylphosphine)palladium(II) chloride (10 mg, 0.01 mmol) in acetonitrile (1 mL) was added aqueous 1M sodium carbonate (1 mL, 1.0 mmol) and the mixture was heated in a microwave at 150° C. for 10 min. The top organic layer was removed, loaded onto a silica gel column and purified by normal phase chromatography (30-100% EtOAc/hexanes) to give 2-(4-quinazolin-8-ylphenyl)-N-{(1R)-1-[5-(2,2,2-trifluoroethoxy)pyridin-2-yl]ethyl}acetamide (21 mg, 38%) as a white solid. $^1$H NMR (400 MHz, CDCl$_3$) δ 9.46 (s, 1H), 9.37 (s, 1H), 8.25 (d, J=2.4 Hz, 1H), 7.96 (m, 2H), 7.75 (m, 1H), 7.69 (d, J=8.2 Hz, 2H), 7.44 (d, J=8.2 Hz, 2H), 7.22 (m, 2H), 6.79 (d, J=7.2 Hz, 1H), 5.16 (m, 1H), 4.37 (q, J=8.0 Hz, 2H), 3.68 (s, 2H), 1.44 (d, J=6.8 Hz, 3H); MS (Electrospray): m/z 467.1 (M$^+$H). FLIPR alpha1I IP=19 nM.

Example 2

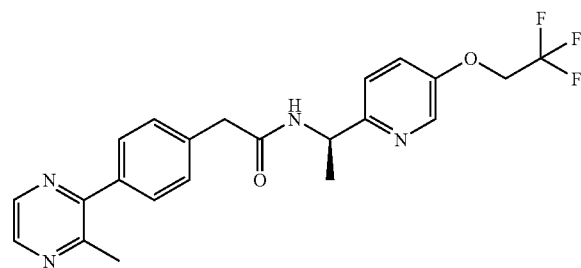 [SMILES: Cc1nccnc1-c1ccc(CC(=O)N[C@H](C)c2ccc(OCC(F)(F)F)cn2)cc1]

2-[4-(3-methylpyrazin-2-yl)phenyl]-N-{(1R)-1-[5-(2,2,2-trifluoroethoxy)pyridin-2-yl]ethyl}acetamide To a solution of 1.00 g (2.15 mmol) 2-[4-(4,4,5,5-tetramethyl-1,3,2-dioxaborolan-2-yl)phenyl]-N-{(1R)-1-[5-(2,2,2-trifluoroethoxy)pyridin-2-yl]ethyl}acetamide in 5.70 ml dioxane was added 0.31 g (2.58 mmol) 2-chloro-3-methylpyrazine, 0.014 mg (0.052 mmol) tricyclohexylphosphine, 0.020 g (0.022 mmol) Pd$_2$dba$_3$, and 2.88 mL (3.66 mmol) 1.7M potassium phosphate. The resulting suspension was degassed for 10mins. After 30 min in the microwave at 150° C., the reaction mixture was cooled, extracted with ethyl acetate, and washed with brine. The organic layer was dried over NaSO$_4$, filtered and concentrated in vacuo. Purification by flash chromatography (silica gel, linear gradient 30-100% EtOAc:hexane) followed by purification by reverse phase chromatography afforded 0.68 g (73.3%) 2-[4-(3-methylpyrazin-2-yl)phenyl]-N-{(1R)-1-[5-(2,2,2-trifluoroethoxy)pyridin-2-yl]ethyl}acetamide. $^1$H NMR (CDCl$_3$, 400 MHz) 8.49 (d, 1H, J=2.20 Hz); 8.45 (d, 1H, J=2.38 Hz); 8.21 (d, 1H, J=2.39 Hz); 7.57 (d, 2H, J=8.24 Hz); 7.41 (d, 2H, J=7.83 Hz); 7.24-7.17 (m, 2H); 6.73 (br d, 1H, J=7.33 Hz); 5.13 (m, 1H); 4.38 (q, 2H, J=8.05 Hz); 3.67 (s, 2H); 2.65 (s, 3H); 1.41 (d, 3H, J=6.77). FlRMS (ES) exact mass calcd for C$_{22}$H$_{21}$F$_3$N$_4$O$_2$: 431.1689, Found: 431.1690. FLIPR alpha1I IP=24 nM.

Example 3

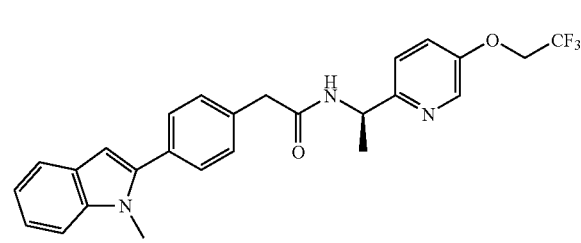 [SMILES: C[C@@H](NC(=O)Cc1ccc(-c2cc3ccccc3n2C)cc1)c1ccc(OCC(F)(F)F)cn1]

2-[4-(1-Methyl-1H-indol-2-yl)phenyl]-N-{(1R)-1-[5-(2,2,2-trifluoroethoxy)pyridin-2-yl]ethyl}acetamide To a mixture of (1-methyl-1H-indol-2-yl)boronic acid (37.7 mg mg, 0.215 mmol), 2-(4-iodophenyl)-N-{(1R)-1-[5-(2,2,2-trifluoroethoxy)pyridin-2-yl]ethyl}acetamide (50.0 mg, 0.108 mmol), tricyclohexylphosphine (0.7 mg, 0.003 mmol), 1-hydroxy-7-azabenzotriazole (101 mg, 0.744 mmol) and Pd$_2$(dba)$_3$ (1 mg, 0.001 mmol) were added dioxane (0.4 mL) and a solution of K3PO4 in H2O (0.2 mL, 1.27 M). The resulting solution was heated in microwave at 150° C. for 0.5 hr. The reaction was completed and diluted with EtOAc. The water later was removed. The remaining organic phase was dried over Na$_2$SO$_4$, filtered and concentrated. The residue was purified by reverse-phase HPLC to give the product as a TFA salt (40 mg, 79%). $^1$H NMR (CDCl$_3$, 400 MHz) δ 8.22 (dd, J=0.8, 2.8 Hz, 1H), 7.63 (d, J=8.0 Hz, 1H), 7.49 (dd, J=2.0, 6.4 Hz, 2H), 7.38 (d, J=8.0 Hz, 2H), 7.37 (d, J=6.4, 1H), 7.27-7.19 (m, 2H), 7.14 (t, J=8.0 Hz, 1H), 6.80 (d, J=7.2 Hz, 1H), 6.56 (s, 1H), 5.14 (quintet, J=7.2 Hz, 1H), 4.38 (q, J=8.0 Hz, 2H), 3.75 (s, 3H), 3.65 (s, 2H), 1.44 (d, J=6.8 Hz, 3H); HRMS (ES) [M+1]$^+$ calcd for C$_{26}$H$_{25}$F$_3$N$_3$O$_2$: 468.1893, Found: 468.1889. FLIPR alpha1I IP=36 nM.

Example 4

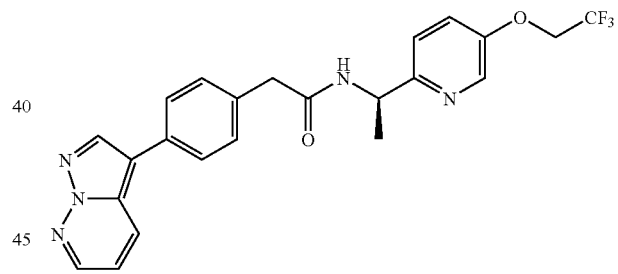

2-(4-Pyrazolo[1,5-b]pyridazin-3-ylphenyl)-N-{(1R)-1-[5-(2,2,2-trifluoroethoxy)pyridin-2-yl]ethyl}acetamide To a solution of 0.69 g (2.74 mmol) (4-pyrazolo[1,5-b]pyridazin-3-ylphenyl)acetic acid in 10.0 ml CH$_2$Cl$_2$ was added 0.96 g (3.28 mmol) of 2-[(1R)-1-ammonioethyl]-5-(2,2,2-trifluoroethoxy)pyridinium dichloride, 0.48 g (3.56 mmol) of HOAt, 0.68 g (3.56 mmol) of EDC, and 1.43 mL (8.21 mmol) of DIEA. After 1 h at room temperature, the reaction mixture was diluted with CH$_2$Cl$_2$, washed three times with water, and washed with brine. The organic layer was dried over Na$_2$SO$_4$, filtered and concentrated in vacuo. Purification by flash chromatography (silica gel, gradient 0-100% EtOAc in hexanes) afforded 0.85 g (68%) of 2-(4-pyrazolo[1,5-b]pyridazin-3-ylphenyl)-N-{(1R)-1-[5-(2,2,2- trifluoroethoxy)pyridin-2-yl]ethyl}acetamide. ¹H NMR (CD₃OD, 400 MHz) 8.40 (m, 2-H); 8.28 (s, 1H); 8.27 (d, J=2.93 Hz, 1H); 7.61 (dd, J=1.83, 6.41 Hz, 2H); 7.43 (m, 3H); 7.31 (d, J=8.61 Hz, 1H); 7.22 (dd, J=4.58, 9.07 Hz, 1H); 5.04 (quintet, J=6.86 Hz, 1H); 4.62 (q, J=8.43 Hz, 2H); 3.61 (s, 2H); 1.46 (d, J=7.05 Hz, 31-1). HRMS (ES) [M+1]⁺calcd for C₂₃H₂₁F₃N₅O₂: 456.1647, Found: 456.1652. FLEPR alpha1I IP=5.0 nM.

Example 5

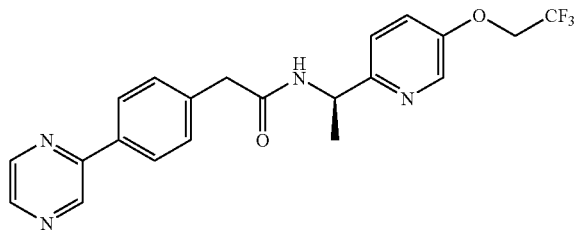 [SMILES: C[C@@H](NC(=O)Cc1ccc(-c2cnccn2)cc1)c1ccc(OCC(F)(F)F)cn1]

2-(4-Pyrazin-2-ylphenyl)-N-{(1R)-1-[5-(2,2,2-trifluoroethoxy)pyridin-2-yl]ethyl}acetamide To a solution of 0.10 g (0.48 mmol) (4-pyrazin-2-ylphenyl) acetic acid in 2.00 ml of CH₂Cl₂ was added 0.17 g (0.58 mmol) of 2-[(1R)-1-ammonioethyl]-5-(2,2,2-trifluoroethoxy)pyridinium dichloride, 0.085 g (0.63 mmol) of HOAt, 0.12 g (0.63 mmol) of EDC, and 0.25 mL (1.44 mmol) of DIEA. After 1 h at room temperature, the reaction mixture was diluted with CH₂Cl₂, washed three times with water, and washed with brine. The organic layer was dried over Na₂SO₄, filtered and concentrated in vacuo. Purification by flash chromatography (silica gel, linear gradient 50-100% EtOAc in hexanes) afforded 0.14 g (70%) of 2-(4-pyrazin-2-ylphenyl)-N-{(1R)-1-[5-(2,2,2-trifluoroethoxy)pyridin-2-yl]ethyl}acetamide. ¹H NMR (CD₃OD, 400 MHz) 9.09 (d, J=1.46 Hz, 1H); 8.65 (t, J=1.74 Hz, 1H); 8.51 (d, J=2.57 Hz, 1H); 8.26 (d, J=3.02 Hz, 1H); 8.03 (d, J=8.15 Hz, 2H); 7.46 (d, J=8.15 Hz, 2H); 7.43 (dd, J=3.02, 8.70 Hz, 1H); 7.30 (d, J=8.70 Hz, 1H); 5.03 (quintet, J=6.96 Hz, 1H); 4.62 (q, J=8.34 Hz, 2H); 3.64 (s, 2H); 1.46 (d, 3H, J=6.96 Hz). HRMS (ES) [M+1]⁺calcd for C₂₁H₂₀F₃N₄O₂: 417.1538, Found: 417.1523. FLIPR alpha1I IP=30 nM.

Example 6

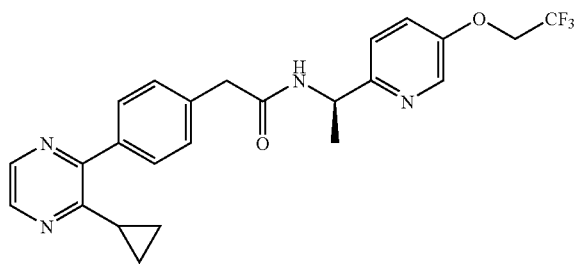 [SMILES: C[C@@H](NC(=O)Cc1ccc(-c2nccnc2C2CC2)cc1)c1ccc(OCC(F)(F)F)cn1]

2-[4-(3-Cyclopropylpyrazin-2-yl)phenyl]-N-{(1R)-1-[5-(2,2,2-trifluoroethoxy)pyridin-2-yl]ethyl}acetamide To a solution of 0.080 g (0.32 mmol) of ([4-(3-cyclopropylpyrazin-2-yl)phenyl]acetic acid in 1.00 ml DMF was added 0.11 g (0.38 mmol) of 2-[(1R)-1-ammonioethyl]-5-(2,2,2-trifluoroethoxy)pyridinium dichloride, 0.056 g (0.41 mmol) of HOAt, 0.078 g (0.41 mmol) of EDC, and 0.17 mL (0.94 mmol) of DIEA. After 12 h at room temperature, the reaction mixture was purified by reverse-phase preparative HPLC (5->95% CH₃CN/H₂O over 15 min, 0.05% added TFA, C18) to afford 0.13 g (73.8%) of 2-[4-(3-cyclopropylpyrazin-2-yl)phenyl]-N-{(1R)-1-[5-(2,2,2-trifluoroethoxy) pyridin-2-yl]ethyl}acetamide. ¹H NMR (CDCl₃, 400 MHz) δ 8.36 (s, 2H); 8.27 (d, J=2.74 Hz, 1H); 7.68 (d, J=8.15 Hz, 2H); 7.40 (d, J=8.06 Hz, 2H); 7.34 (m, 2H); 7.20 (d, J=5.95 Hz, 1H); 5.15 (m, 1H); 4.41 (dd, J=7.88, 15.84 Hz, 2H); 3.65 (s, 2H); 2.22 (m, 1H); 1.46 (d, J=6.95 Hz, 3H); 1.19 (m, 2H); 0.99 (m, 2H). HRMS (ES) [M+1]⁺calcd for C₂₄H₂₄F₃N₄O₂: 457.1851, Found: 457.1831. FLIPR alpha1I IP=47 nM.

Example 7

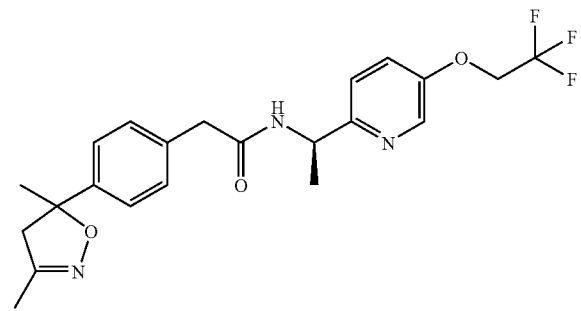 [SMILES: CC1=NOC(C)(c2ccc(CC(=O)N[C@H](C)c3ccc(OCC(F)(F)F)cn3)cc2)C1]

2-[4-(3,5-Dimethyl-4,5-dihydro-isoxazol-5-yl)phenyl]-N-{(1R)-1-[5-(2,2,2-trifluoroethoxy)pyridin-2-yl]ethyl}acetamide To a solution of acetaldoxime (14.1 mg, 0.238 mmol) was added N-chlorosuccinimide (31.8 mg, 0.238 mmol). The resulting mixture was stirred at room temperature for 3 h. 2-(4-Isopropenylphenyl)-N-{(1R)-1-[5-(2,2,2-trifluoroethoxy)pyridin-2-yl]ethyl}acetamide (90 mg, 0.24 mmol) was added, followed by the TEA (0.099 ml, 0.71 mmol), the resulting mixture was stirred at room temperature for 24 h. The reaction mixture was washed with saturated sodium bicarbonate solution and brine. Organics were extracted with CH₂Cl₂, dried over Na₂SO₄, filtered and concentrated in vacuo. Purification by reverse phase chromatography gave 2-[4-(3,5-dimethyl-4,5-dihydro-isoxazol-5-yl)phenyl]-N-{(1R)-1-[5-(2,2,2-trifluoroethoxy)pyridin-2-yl]ethyl}acetamide as a white solid (23.8 mg, 23%). ¹H NMR (CDCl₃, 400 MHz). δ 8.299 (dd, J=2.75, 5.31 Hz, 1H); 7.407 (t, J=2.93 Hz, 1H); 7.361 (dd, J=1.28 Hz, J=8.42 Hz, 4H); 7.243 (d, J=2.20 Hz, 1H); 7.222 (d, J=2.38 Hz, 1H); 5.122 (quintet, J=7.14 Hz, 1H); 4.436 (m, 2H); 3.550 (s, 2H); 3.063 (m, 2H); 1.965 (t, J=1.10 Hz, 3H); 1.684 (d, J=1.10 Hz, 2H); 1.466 (d, J=6.96 Hz, 3H); MS (ES): m/z 436.2 (M+H). FLIPR alpha1I IP=41 nM.

Example 8

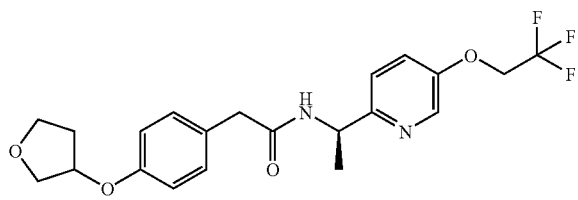 [SMILES: C[C@@H](NC(=O)Cc1ccc(OC2CCOC2)cc1)c1ccc(OCC(F)(F)F)cn1]

2-[4-(Tetrahydrofuran-3-yloxy)phenyl]-N-((1R)-1-{5-[(2,2,2-trifluoroethyl)amino]pyridin-2-yl}ethyl)acetamide To a solution of the starting 2-(4-hydroxyphenyl)-N-((1R)-1-{5-[(2,2,2-trifluoroethyl)amino]pyridin-2-yl}ethyl)acetamide (60 mg, 0.17 mmol) in 0.5 ml of dry THF was added the 3-Hydroxytetrahydrofuran (14.92 mg, 0.169 mmol), Di-tert-butyl azodicarboxylate (58.5 mg, 0.254 mmol) and triphenylphosphine (66.6 mg, 0.254 mmol). The mixture was stirred at room temperature for Overnight. The reaction mixture was washed with saturated sodium bicarbonate solution and brine. Organics were extracted with $CH_2Cl_2$, dried over $Na_2SO_4$, filtered and concentrated in vacuo. Purification by reverse phase chromatography gave 2-[4-(tetrahydrofuran-3-yloxy)phenyl]-N-((1R)-1-{5-[(2,2,2-trifluoroethyl)amino]pyridin-2-yl}ethyl)acetamide as a white solid (0.050 g, 70%). $^1$H NMR ($CDCl_3$, 400 MHz) δ 8.212 (d, J=2.38 Hz, 1H); 7.189 (m, 4H); 6.830 (m, 2H); 6.624 (d, J=7.15 Hz, 1H); 5.103 (quintet, J=6.95 Hz, 1H); 4.924 (m, 1H); 4.379 (dd, J=8.06, 15.93 Hz, 2H); 3.999 (m, 3H); 3.905 (m, 1H); 3.519 (s, 2H); 2.187 (m, 2H); 1.387 (d, J=6.78 Hz, 3H); MS (ES): m/z 425.2 (M+H). FLIPR alpha1I IP=91 nM.

Example 9

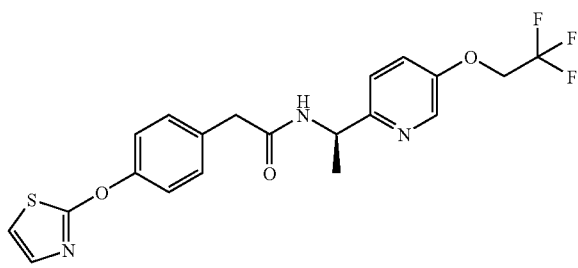 [SMILES: C[C@@H](NC(=O)Cc1ccc(Oc2nccs2)cc1)c1ccc(OCC(F)(F)F)cn1]

2-[4-(1,3-Thiazol-2-yloxy)phenyl]-N-((1R)-1-{5-[(2,2,2-trifluoroethyl)amino]pyridin-2-yl}ethyl)acetamide To a solution of the starting 2-(4-hydroxyphenyl)-N-((1R)-1-{5-[(2,2,2-trifluoroethyl)amino]pyridin-2-yl}ethyl)acetamide (60.0 mg, 0.17 mmol) in 1.0 ml of dry DMF was added the 2-bromo-1,3-thiazole (30.6 mg, 0.186 mmol), $Cs_2CO_3$ (166 mg, 0.508 mmol), and copper powder (1.1 mg, 0.017 mmol). The mixture was irradiated with microwave at 100° C. for 1 h. The mixture was cooled, diluted with $CH_2Cl_2$, and washed with saturated sodium bicarbonate solution and brine. The combined aqueous washes were extracted with $CH_2Cl_2$. The combined organic phase was dried over $Na_2SO_4$, filtered and concentrated in vacuo. Purification by reverse phase chromatography gave 2-[4-(1,3-thiazol-2-yloxy)phenyl]-N-((1R)-1-{5-[(2,2,2-trifluoroethyl)amino]pyridin-2-yl}ethyl)acetamide as a white solid (18 mg, 24%). $^1$H NMR ($CDCl_3$, 400 MHz) δ 8.227 (d, J=2.75 Hz, 1H); 7.329 (m, 2H); 7.242 (m, 5H); 6.825 (d, J=2.85 Hz, 1H); 6.765 (d, J=7.14 Hz, 1H); 5.106 (quintet, J=6.84 Hz, 1H); 4.381 (dd, J=7.87, 15.93 Hz, 2H); 3.592 (s, 2H); 1.411 (d, J=6.78 Hz, 3H); MS (ES): m/z 438.1 (M+H). FLIPR alpha1I IP=46 nM.

Example 10

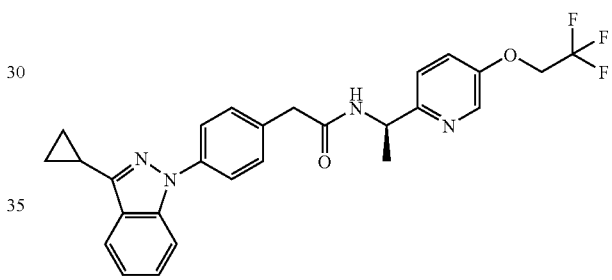

2-[4-(3-Cyclopropyl-1H-indazole-1-yl)phenyl]-N-((1R)-1-{5-[(2,2,2-trifluoroethyl)amino]-pyridin-2-yl}ethyl)acetamide The starting 2-(4-iodophenyl)-N-((1R)-1-{5-[(2,2,2-trifluoroethyl)amino]pyridin-2-yl}ethyl)acetamide (130 mg, 0.280 mmol), 3-cyclopropyl-1H-indazole (66.5 mg, 0.420 mmol), copper (I) oxide (2.004 mg, 0.014 mmol), cesium carbonate (146 mg, 0.448 mmol), and salicylaldoxime (7.68 mg, 0.056 mmol) were mixed into 1.0 ml of $CH_3CN$ in a sealed bottle. The mixture was stirred at 150° C. overnight. After cooled, water (25 mL) was added and the mixture. Organics were extracted with $CH_2Cl_2$, dried over $Na_2SO_4$, filtered and concentrated in vacuo. The residue was purified by silica gel chromatography (gradient, 30-100% EtOAc in hexanes) to give 2-[4-(3-cyclopropyl-1H-indazole-1-yl)phenyl]-N-((1R)-1-{5-[(2,2,2-trifluoroethyl)amino]pyridin-2-yl}ethyl)acetamide as a light yellow solid (94 mg, 68%). $^1$H NMR ($CDCl_3$, 400 MHz) δ 8.206 (d, J=2.57 Hz, 1H); 7.816 (d, J=8.06 Hz, 1H); 7.683 (m, 3H); 7.407 (m, 3H); 7.208 (m, 3H); 6.726 (d, J=7.14 Hz, 1H); 5.128 (quintet, J=6.96 Hz, 1H); 4.361 (dd, J=15.93, 7.96 Hz, 2H); 3.645 (s, 2H); 2.288 (m, 1H); 1.413 (d, J=6.77 Hz, 3H); 1.175 (m, 2H); 1.085 (m, 2H); MS (ES): m/z 495.2 (M+H). FLIPR alpha1I IP=73 nM.

TABLE 1

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 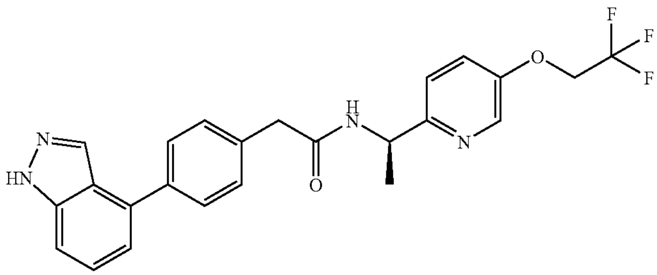 [SMILES: C[C@@H](NC(=O)Cc1ccc(-c2cccc3[nH]ncc23)cc1)c1ccc(OCC(F)(F)F)cn1] | 2-[4-(1H-indazol-4-yl)phenyl]-N-{(1R)-1-[5-(2,2,2-trifluoroethoxy)pyridin-2-yl]ethyl}acetamide | 455.1 |
| 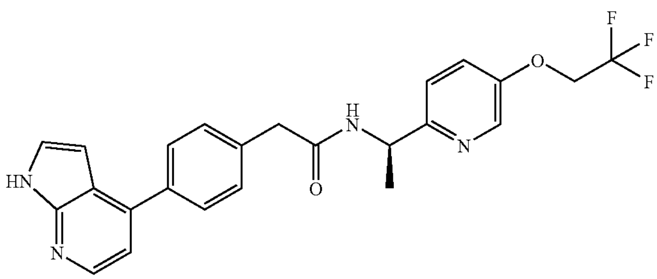 | 2-[4-(1H-pyrrolo[2,3-b]pyridin-4-yl)phenyl]-N-{(1R)-1-[5-(2,2,2-trifluoroethoxy)pyridin-2-yl]ethyl}acetamide | 455.2 |
| 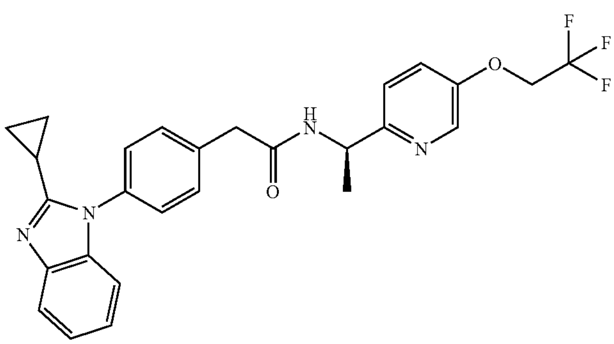 [SMILES: C[C@@H](NC(=O)Cc1ccc(-n2c(C3CC3)nc3ccccc32)cc1)c1ccc(OCC(F)(F)F)cn1] | 2-[4-(2-cyclopropyl-1H-benzimidazol-1-yl)phenyl]-N-{(1R)-1-[5-(2,2,2-trifluoroethoxy)pyridin-2-yl]ethyl}acetamide | 495.1 |
| 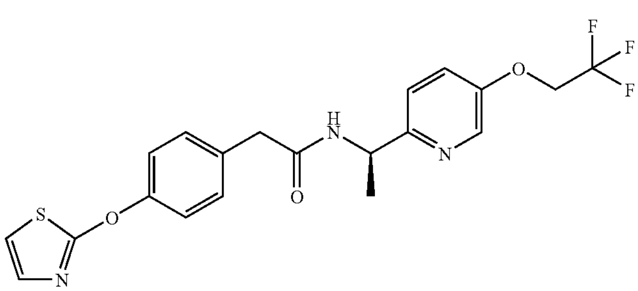 [SMILES: C[C@@H](NC(=O)Cc1ccc(Oc2nccs2)cc1)c1ccc(OCC(F)(F)F)cn1] | 2-[4-(1,3-thiazol-2-yloxy)phenyl]-N-{(1R)-1-[5-(2,2,2-trifluoroethoxy)pyridin-2-yl]ethyl}acetamide | 438.1 |
| 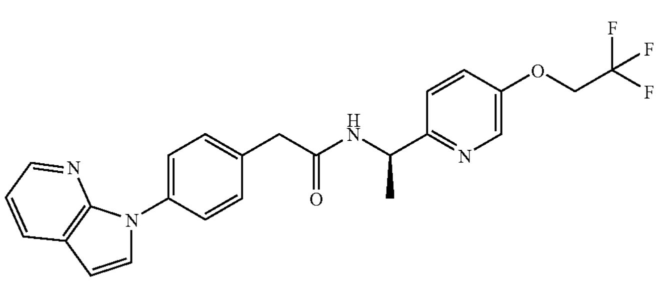 [SMILES: C[C@@H](NC(=O)Cc1ccc(-n2ccc3cccnc32)cc1)c1ccc(OCC(F)(F)F)cn1] | 2-[4-(1H-pyrrolo[2,3-b]pyridin-1-yl)phenyl]-N-{(1R)-1-[5-(2,2,2-trifluoroethoxy)pyridin-2-yl]ethyl}acetamide | 455.2 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 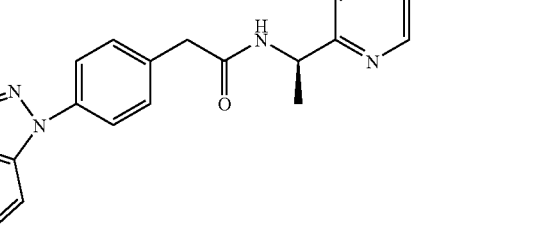 | 2-[4-(3-cyclopropyl-1H-indazol-1-yl)phenyl]-N-{(1R)-1-[5-(2,2,2-trifluoroethoxy)pyridin-2-yl]ethyl}acetamide | 495.2 |
| 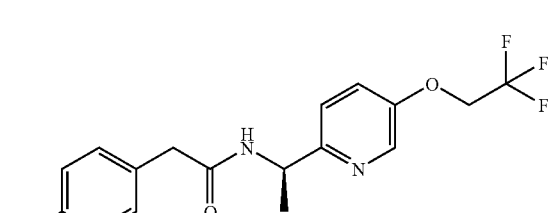 | 2-[4-(3-oxo[1,2,4]triazolo[4,3-a]pyridin-2(3H)-yl)phenyl]-N-{(1R)-1-[5-(2,2,2-trifluoroethoxy)pyridin-2-yl]ethyl}acetamide | 472.1 |
| 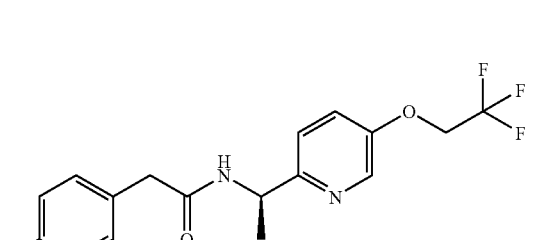 | 2-[4-(tetrahydrofuran-3-yloxy)phenyl]-N-{(1R)-1-[5-(2,2,2-trifluoroethoxy)pyridin-2-yl]ethyl}acetamide | 425.1 |
| 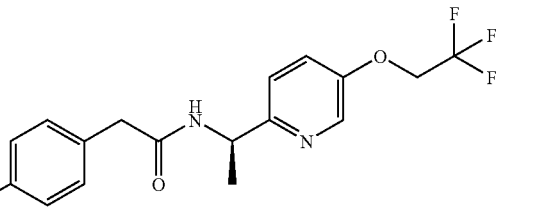 | 2-[4-(7H-pyrrolo[2,3-d]pyrimidin-4-yl)phenyl]-N-{(1R)-1-[5-(2,2,2-trifluoroethoxy)pyridin-2-yl]ethyl}acetamide | 456.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 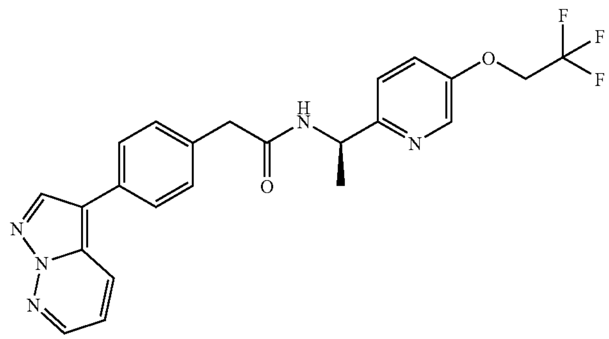 [SMILES: C[C@@H](NC(=O)Cc1ccc(-c2cnn3ncccc23)cc1)c1ccc(OCC(F)(F)F)cn1] | 2-(4-pyrazolo[1,5-b]pyridazin-3-ylphenyl)-N-{(1R)-1-[5-(2,2,2-trifluoroethoxy)pyridin-2-yl]ethyl}acetamide | 456.1 |
| 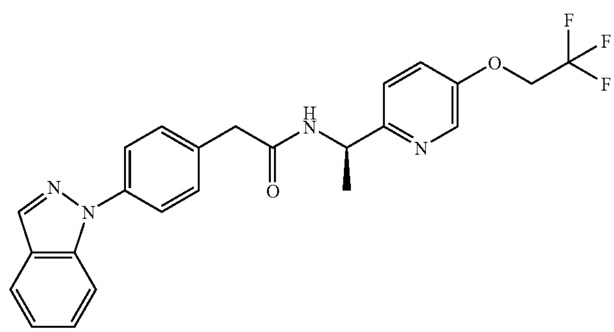 [SMILES: C[C@@H](NC(=O)Cc1ccc(-n2ncc3ccccc32)cc1)c1ccc(OCC(F)(F)F)cn1] | 2-[4-(1H-indazol-1-yl)phenyl]-N-{(1R)-1-[5-(2,2,2-trifluoroethoxy)pyridin-2-yl]ethyl}acetamide | 455.1 |
| 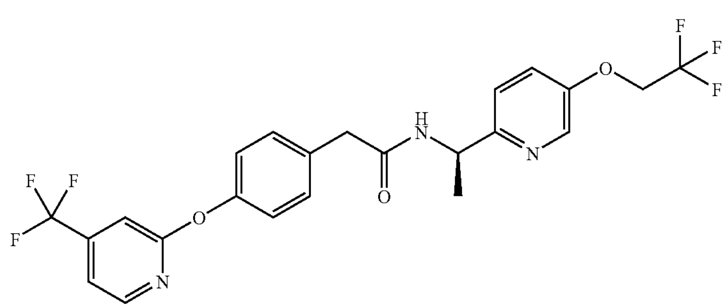 [SMILES: C[C@@H](NC(=O)Cc1ccc(Oc2cc(C(F)(F)F)ccn2)cc1)c1ccc(OCC(F)(F)F)cn1] | N-{(1R)-1-[5-(2,2,2-trifluoroethoxy)pyridin-2-yl]ethyl}-2-(4-{[4-(trifluoromethyl)pyridin-2-yl]oxy}phenyl)acetamide | 500.1 |
| 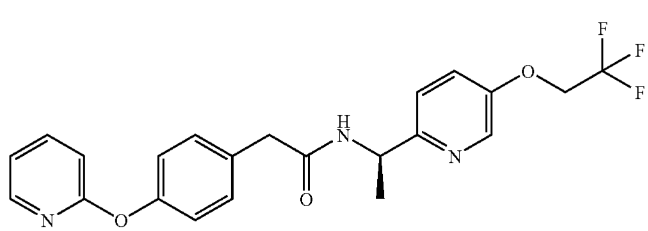 [SMILES: C[C@@H](NC(=O)Cc1ccc(Oc2ccccn2)cc1)c1ccc(OCC(F)(F)F)cn1] | 2-[4-(pyridin-2-yloxy)phenyl]-N-{(1R)-1-[5-(2,2,2-trifluoroethoxy)pyridin-2-yl]ethyl}acetamide | 432.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 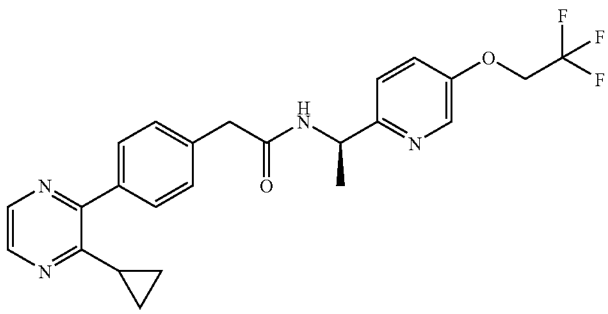 [SMILES: C[C@@H](NC(=O)Cc1ccc(-c2nccnc2C2CC2)cc1)c1ccc(OCC(F)(F)F)cn1] | 2-[4-(3-cyclopropylpyrazin-2-yl)phenyl]-N-{(1R)-1-[5-(2,2,2-trifluoroethoxy)pyridin-2-yl]ethyl}acetamide | 457.2 |
| 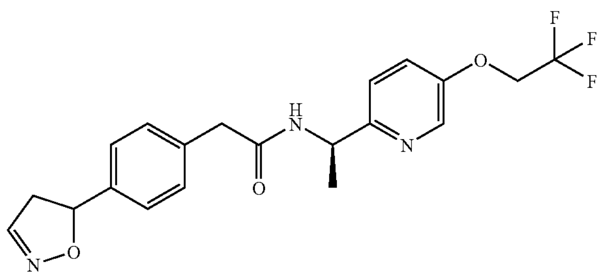 [SMILES: C[C@@H](NC(=O)Cc1ccc(C2CC=NO2)cc1)c1ccc(OCC(F)(F)F)cn1] | 2-[4-(4,5-dihydroisoxazol-5-yl)phenyl]-N-{(1R)-1-[5-(2,2,2-trifluoroethoxy)pyridin-2-yl]ethyl}acetamide | 408.1 |
| 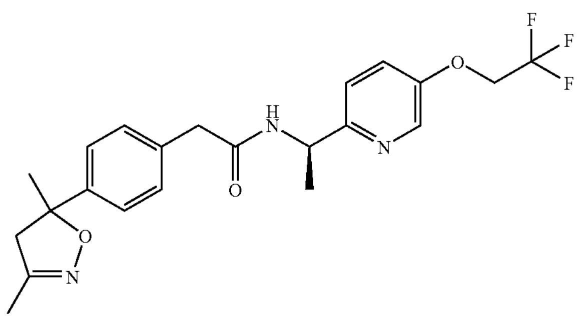 [SMILES: CC1=NOC(C)(c2ccc(CC(=O)N[C@H](C)c3ccc(OCC(F)(F)F)cn3)cc2)C1] | 2-[4-(3,5-dimethyl-4,5-dihydroisoxazol-5-yl)phenyl]-N-{(1R)-1-[5-(2,2,2-trifluoroethoxy)pyridin-2-yl]ethyl}acetamide | 436.2 |
| 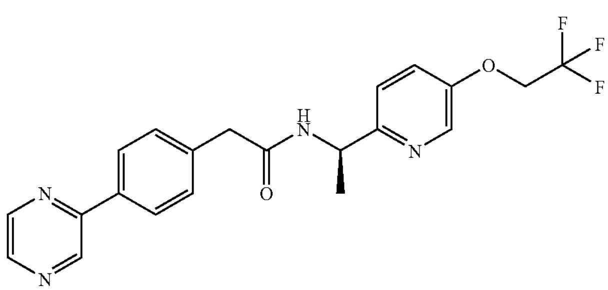 [SMILES: C[C@@H](NC(=O)Cc1ccc(-c2cnccn2)cc1)c1ccc(OCC(F)(F)F)cn1] | 2-(4-pyrazin-2-ylphenyl)-N-{(1R)-1-[5-(2,2,2-trifluoroethoxy)pyridin-2-yl]ethyl}acetamide | 417.1 |
| 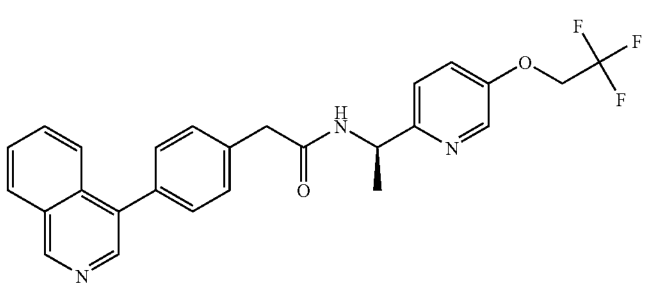 [SMILES: C[C@@H](NC(=O)Cc1ccc(-c2cncc3ccccc23)cc1)c1ccc(OCC(F)(F)F)cn1] | 2-(4-isoquinolin-4-ylphenyl)-N-{(1R)-1-[5-(2,2,2-trifluoroethoxy)pyridin-2-yl]ethyl}acetamide | 466.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 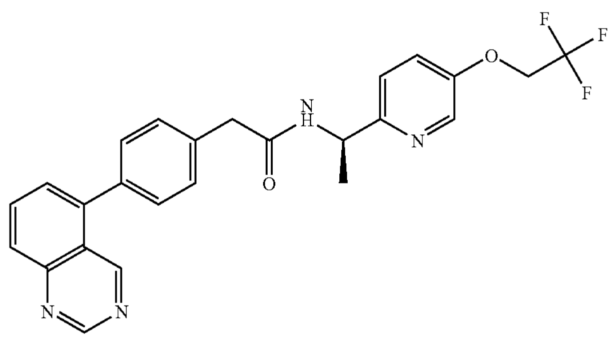 [SMILES: C[C@@H](NC(=O)Cc1ccc(-c2cccc3ncncc23)cc1)c1ccc(OCC(F)(F)F)cn1] | 2-(4-quinazolin-5-ylphenyl)-N-{(1R)-1-[5-(2,2,2-trifluoroethoxy)pyridin-2-yl]ethyl}acetamide | 467.1 |
| 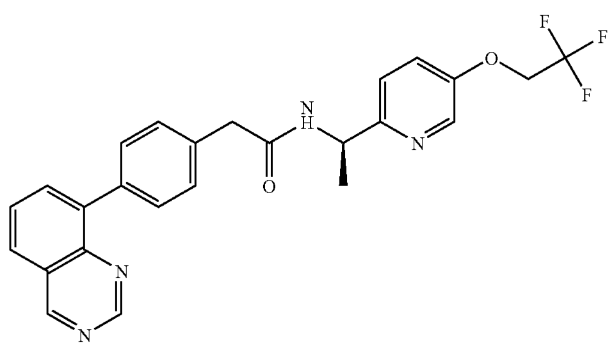 [SMILES: C[C@@H](NC(=O)Cc1ccc(-c2cccc3cncnc23)cc1)c1ccc(OCC(F)(F)F)cn1] | 2-(4-quinazolin-8-ylphenyl)-N-{(1R)-1-[5-(2,2,2-trifluoroethoxy)pyridin-2-yl]ethyl}acetamide | 467.1 |
| 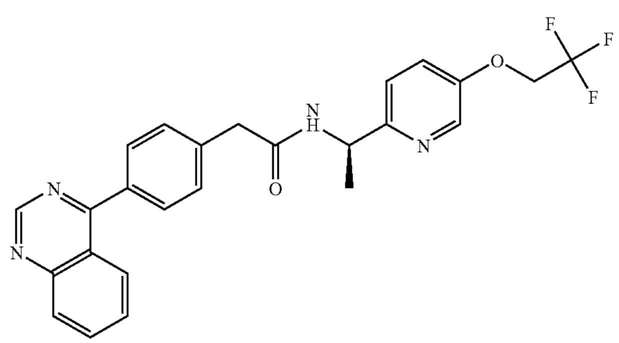 | 2-(4-quinazolin-4-ylphenyl)-N-{(1R)-1-[5-(2,2,2-trifluoroethoxy)pyridin-2-yl]ethyl}acetamide | 467.1 |
| 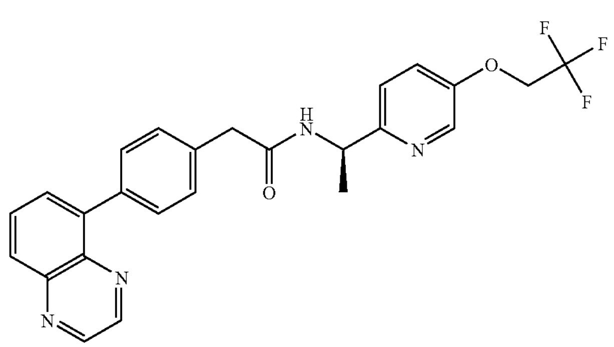 [SMILES: C[C@@H](NC(=O)Cc1ccc(-c2cccc3nccnc23)cc1)c1ccc(OCC(F)(F)F)cn1] | 2-(4-quinoxalin-5-ylphenyl)-N-{(1R)-1-[5-(2,2,2-trifluoroethoxy)pyridin-2-yl]ethyl}acetamide | 467.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 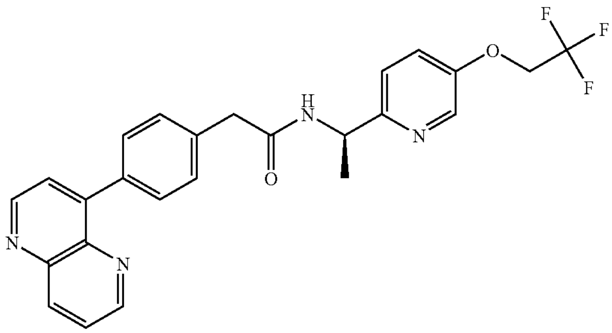 [SMILES: C[C@@H](NC(=O)Cc1ccc(-c2ccnc3cccnc23)cc1)c1ccc(OCC(F)(F)F)cn1] | 2-[4-(1,5-naphthyridin-4-yl)phenyl]-N-{(1R)-1-[5-(2,2,2-trifluoroethoxy)pyridin-2-yl]ethyl}acetamide | 467.1 |
| 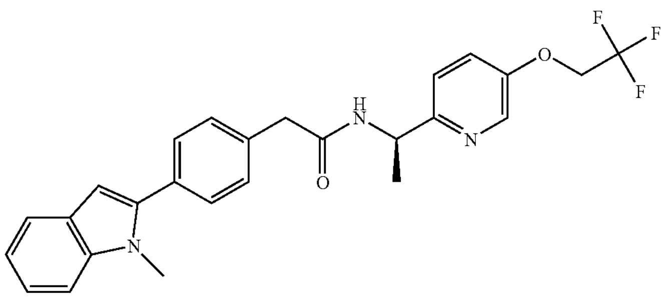 [SMILES: C[C@@H](NC(=O)Cc1ccc(-c2cc3ccccc3n2C)cc1)c1ccc(OCC(F)(F)F)cn1] | 2-[4-(1-methyl-1H-indol-2-yl)phenyl]-N-{(1R)-1-[5-(2,2,2-trifluoroethoxy)pyridin-2-yl]ethyl}acetamide | 468.2 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula Id:

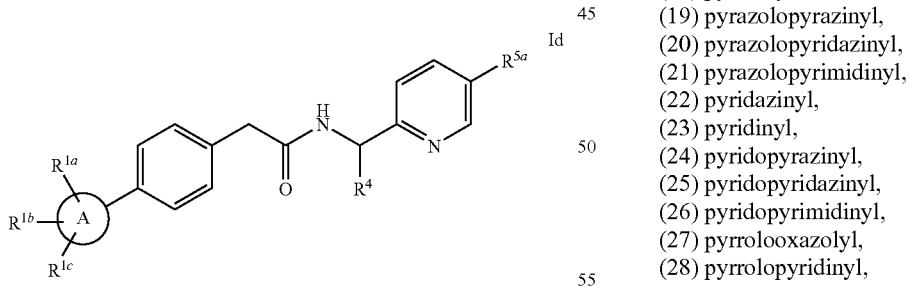

wherein:

A is selected from the group consisting of:
(1) benzimidazolyl,
(2) benzofuranyl,
(3) dihydroisoxazolyl,
(4) dihydropyrrolopyrrolyl,
(5) furopyridinyl,
(6) furopyrrolyl,
(7) imidazopyrazinyl,
(8) imidazopyridazinyl,
(9) imidazopyridinyl,
(10) imidazopyrimidinyl,
(11) indazolyl,
(12) indolizinyl;
(13) indolyl,
(14) isoindolyl,
(15) isoquinolinyl,
(16) naphthyrindinyl,
(17) oxotriazolopyridinyl,
(18) pyrazinyl,
(19) pyrazolopyrazinyl,
(20) pyrazolopyridazinyl,
(21) pyrazolopyrimidinyl,
(22) pyridazinyl,
(23) pyridinyl,
(24) pyridopyrazinyl,
(25) pyridopyridazinyl,
(26) pyridopyrimidinyl,
(27) pyrrolooxazolyl,
(28) pyrrolopyridinyl,
(29) pyrrolopyrimidinyl,
(30) quinazolinyl,
(31) quinolinyl,
(32) quinoxalinyl,
(33) tetrahydrofuranyl,
(34) thiazolyl,
(35) triazolopyrazinyl,
(36) triazolopyridazinyl,
(37) triazolopyridinyl, and
(38) triazolopyrimidinyl;

$R^{1a}$, $R^{1b}$ and $R^{1c}$ are independently selected from the group consisting of:

51

(1) hydrogen,
(2) halogen,
(3) phenyl or napthyl, which is unsubstituted or substituted with halogen, hydroxyl, $C_{1-6}$alkyl, —O-$C_{1-6}$alkyl, $C_{3-6}$cycloalkyl, —SH, —S-$C_{1-6}$alkyl, —NO$_2$, —CO$_2$H, or —CN,
(4) —O-phenyl, which is unsubstituted or substituted with halogen, hydroxyl, $C_{1-6}$alkyl, —O-$C_{1-6}$alkyl, —SH, —S-$C_{1-6}$alkyl, —NO$_2$, —CO$_2$H, or —CN,
(5) $C_{1-6}$alkyl, which is unsubstituted or substituted with halogen, hydroxyl, phenyl or —O-$C_{1-6}$alkyl,
(6) $C_{3-6}$cycloalkyl, which is unsubstituted or substituted with halogen, hydroxyl, phenyl or —O-$C_{1-6}$alkyl,
(7) $C_{2-4}$alkenyl, which is unsubstituted or substituted with $C_{3-6}$cycloalkyl or phenyl,
(8) —NR$^{10}$R$^{11}$, wherein R$^{10}$ and R$^{11}$ are independently selected from hydrogen and $C_{1-6}$alkyl,
(9) isoxazolyl, which is unsubstituted or substituted with $C_{1-6}$alkyl,
(10) imidazolyl, which is unsubstituted or substituted with $C_{1-6}$alkyl,
(11) morpholinyl, which is unsubstituted or substituted with $C_{1-6}$alkyl,
(12) oxazolyl, which is unsubstituted or substituted with $C_{1-6}$alkyl,
(13) pyrazolyl, which is unsubstituted or substituted with $C_{1-6}$alkyl,
(14) pyrrolidinyl, which is unsubstituted or substituted with halogen,
(15) tetrazolyl, which is unsubstituted or substituted with $C_{1-6}$alkyl,
(16) thienyl, which is unsubstituted or substituted with $C_{1-6}$alkyl,
(17) benzothienyl, which is unsubstituted or substituted with $C_{1-6}$alkyl,
(18) triazolyl, which is unsubstituted or substituted with $C_{1-6}$alkyl,
(19) —NO$_2$, and
(20) —CN,
or R$^{1a}$ and R$^{1b}$ taken together form a cyclopentyl, cyclohexyl, dihydrofuranyl or dihydropyranyl ring, which is unsubstituted or substituted with —CH$_3$, (=CH$_2$). keto, or hydroxyl;
R$^4$ is selected from the group consisting of:
(1) CH$_3$,
(2) CH$_2$OH,
(3) CH$_2$OCH$_3$,
(4) CH$_2$CH$_3$,
(5) CH=CH$_2$,
(6) CH$_2$CH$_2$OH,
(7) CH$_2$CH=CH$_2$,
(8) CH$_2$CH$_2$F,
(9) CH$_2$CF$_2$,
(10) CH$_2$-phenyl,
(12) CH$_2$-cyclopropyl,
(13) CH$_2$-cyclobutyl,
(14) cyclopropyl,
(15) cyclobutyl,
(16) CH$_2$CH$_2$CH$_3$, and
(17) —(C=O)—O—CH$_3$;
R$^{5a}$ is independently selected from the group consisting of:
(1) hydrogen,
(2) fluoro,
(3) chloro,
(4) bromo,
(5) hydroxyl,
(6) —CH$_3$,

52

(7) —CH$_2$OH,
(8) —CH$_2$CH$_3$,
(9) —CH$_2$=CH$_2$,
(10) —CH$_2$CH$_2$CH$_3$,
(11) -cyclopropyl
(12) —OCH$_3$,
(13) —OCH$_2$F,
(14) —OCH$_2$-cyclopropyl,
(15) —OCH$_2$-phenyl,
(16) —OCH$_2$CH$_3$,
(17) —OCH$_2$CF$_3$,
(18) —OCH$_2$CH$_2$CH$_3$,
(19) —OCH$_2$(C=O)OCH$_2$CH$_3$, and
(20) —OCH$_2$(C=O)NHCH$_2$CH$_3$;
or a pharmaceutically acceptable salt thereof.

2. The compound of claim 1 wherein R$^4$ is in the (R) orientation.

3. The compound of claim 1 wherein R$^4$ is CH$_3$.

4. A compound which is selected from the group consisting of:

2-(4-quinazolin-8-ylphenyl)-N-{(1R)-1-[5-(2,2,2-trifluoroethoxy)pyridin-2-yl]ethyl}acetamide;

2-[4-(3-methylpyrazin-2-yl)phenyl]-N-{(1R)-1-[5-(2,2,2-trifluoroethoxy)pyridin-2-yl ]ethyl}acetamide;

2-[4-(1-methyl-1H-indo-2-yl)phenyl]-N-{(1R)-1 -[5-(2,2,2-trifluoroethoxy)pyridin-2-yl ]ethyl}acetamide;

2-(4-pyrazolo[1,5-b]pyridazin-3-ylphenyl)-N-{(1R)-1-[5-(2,2,2-trifluoroethoxy)pyridin-2-yl ]ethyl} acetamide;

2-(4-pyrazin-2-ylphenyl)-N-{(1R)-1[5-(2,2,2-trifluoroethoxy)pyridin-2-yl]ethyl}acetamide;

2-[4-(3-cyclopropylpyrazin-2-yl)phenyl]-N-{(1R)-1-[5-(2,2,2-trifluoro ethoxy)pyridin-2-yl ]ethyl}acetamide;

2-[4-(3,5-dimethyl-4,5-dihydro-isoxazol-5-yl)phenyl]-N-{(1R)-1-[5-(2,2,2-trifluoroethoxy) pyridin-2-yl]ethyl}acetamide;

2-[4-(tetrahydrofuran-3-yloxy)phenyl]-N-((1R)-1-{5-[(2,2,2-trifluoroethyl)amino]pyridin-2-yl }ethyl)acetamide;

2-[4-(1,3-thiazol-2-yloxy)phenyl]-N-((1R)-1-{5 -[(2,2,2-trifluoroethyl)amino]pyridin-2-yl }ethyl)acetamide;

2-[4-(3-cyclopropyl-1H-indazole-1-yl)phenyl]-N-((1R)-1-{5-[(2,2,2-trifluoroethyl) amino]pyridin-2-yl}ethyl) acetamide;

2-[4-(1H-indazol-4-yl)phenyl]-N-{(1R)-1-[5-(2,2,2-trifluoroethoxy)pyridin-2-yl ]ethyl}acetamide;

2-[4-(1H-pyrrolo [2,3 -b]pyridin-4-yl)phenyl]-N-{(1R)-1-[5-(2,2,2-trifluoroethoxy)pyridin-2-yl ]ethyl} acetamide;

2-[4-(2-cyclopropyl-1H-benzimidazol-1-yl)phenyl]-N-{(1R)-1-[5-(2,2,2-trifluoroethoxy)pyridin-2-yl] ethyl}acetamide;

2-[4-(1,3-thiazol-2-yloxy)phenyl]-N-{(1R)-1[5-(2,2,2-trifluoroethoxy)pyridin-2-yl ]ethyl}acetamide;

2-[4-(1H-pyrrolo [2,3-b]pyridin-1-yl)phenyl]-N-{(1R)-1-[5-(2,2,2-trifluoroethoxy)pyridin-2-yl ]ethyl} acetamide;

2-[4-(3-cyclopropyl-1H-indazol-1-yl)phenyl]-N-{(1R)-1 [5-(2,2,2-trifluoroethoxy)pyridin-2-yl ]ethyl} acetamide;

2-[4-(3-oxo [1,2,4]triazolo [4,3-a]pyridin-2(3H)-yl)phenyl]-N-{(1R)-1-[5-(2,2,2-trifluoroethoxy) pyridin-2-yl] ethyl}acetamide;

2-[4-(tetrahydrofuran-3-yloxy)phenyl]-N-{(1R)-1[5-(2,2,2-trifluoroethoxy)pyridin-2-yl ]ethyl}acetamide;

2-[4-(7H-pyrrolo[2,3-d]pyrimidin-4-yl)phenyl]-N-{(1R)-1-[5-(2,2,2-trifluoro ethoxy)pyridin-2-yl ]ethyl} acetamide;

2-(4-pyrazolo [1,5-b]pyridazin-3-ylphenyl)-N-{(1R)-1-[5-(2,2,2-trifluoroethoxy)pyridin-2-yl ]ethyl} acetamide;

2-[4-(1H-indazol-1-yl)phenyl]-N-{(1R)-1-[5 -(2,2,2-trifluoroethoxy)pyridin-2-yl ]ethyl}acetamide;

N-{(1R)-1[5-(2,2,2-trifluoroethoxy)pyridin-2-yl]ethyl}-2-(4-{[4-(trifluoromethyl)pyridin-2-yl ]oxy}phenyl)acetamide;

2-[4-(pyridin-2-yloxy)phenyl]-N-{(1R)-1-[5-(2,2,2-trifluoroethoxy)pyridin-2-yl]ethyl}acetamide;

2-[4-(3-cyclopropylpyrazin-2-yl)phenyl]-N-{(1R)-1 [5-(2,2,2-trifluoroethoxy)pyridin-2-yl ]ethyl}acetamide;

2-[4-(4,5-dihydroisoxazol-5-yl)phenyl]-N-{(1R)-1[5-(2,2,2-trifluoroethoxy)pyridin-2-yl ]ethyl}acetamide;

2- [4-(3,5-dimethyl-4,5-dihydroisoxazol-5-yl)phenyl]-N-{(1R)-1[5-(2,2,2-trifluoroethoxy) pyridin-2-yl] ethyl}acetamide;

2-(4-pyrazin-2-ylphenyl)-N-{(1R)-1[5-(2,2,2-trifluoroethoxy)pyridin-2-yl]ethyl}acetamide;

2-(4-isoquinolin-4-ylphenyl)-N-{(1R)-1[5-(2,2,2-trifluoroethoxy)pyridin-2-yl]ethyl}acetamide;

2-(4-quinazolin-5-ylphenyl)-N-{(1R)-1[5-(2,2,2-trifluoroethoxy)pyridin-2-yl]ethyl}acetamide;

2-(4-quinazolin-8-ylphenyl)-N-{(1R)-1[5-(2,2,2-trifluoroethoxy)pyridin-2-yl]ethyl}acetamide;

2-(4-quinazolin-4-ylphenyl)-N-{(1R)-1[5-(2,2,2-trifluoroethoxy)pyridin-2-yl]ethyl}acetamide;

2-(4-quinoxalin-5-ylphenyl)-N-{(1R)-1[5-(2,2,2-trifluoroethoxy)pyridin-2-yl]ethyl}acetamide;

2-[4-(1,5-naphthyridin-4-yl)phenyl]-N-{(1R)-1-[5-(2,2,2-trifluoroethoxy)pyridin-2-yl ]ethyl}acetamide; and 2-[4-(1-methyl-1H-indo2-yl)phenyl]-N-{(1R)-1-[5-(2,2,2-trifluoroethoxy)pyridin-2-yl ]ethyl}acetamide;

or a pharmaceutically acceptable salt thereof.

5. A compound which is 2-[4-(3-methylpyrazin-2-yl) phenyl]-N-{(1R)-1[5-(2,2,2-trifluoroethoxy)pyridin-2-yl]ethyl}acetamide, or a pharmaceutically acceptable salt thereof.

6. The compound of claim 5 which is 2[4(3-methylpyrazin -2-yl)phenyl]-N-{(1R)-1[5-(2,2,2-trifluoroethoxy)pyridin-2-yl]ethyl}acetamide.

7. The compound of claim 5 which is 2-[4-(3-methylpyrazin -2-yl)phenyl]-N-{(1R)-1-[5(2,2,2-trifluoroethoxy) pyridin-2-yl]ethyl}acetamide in the form of a pharmaceutically acceptable salt.

8. A pharmaceutical composition which comprises an inert carrier and a compound of claim 1 or a pharmaceutically acceptable salt thereof.

9. A pharmaceutical composition which comprises an inert carrier and a compound of claim 4 or a pharmaceutically acceptable salt thereof.

10. A pharmaceutical composition which comprises an inert carrier and a compound of claim 5 or a pharmaceutically acceptable salt thereof.

11. A pharmaceutical composition which comprises an inert carrier and a compound of claim 6 or a pharmaceutically acceptable salt thereof.

12. A pharmaceutical composition which comprises an inert carrier and a compound of claim 7 or a pharmaceutically acceptable salt thereof.

* * * * *